(12) United States Patent
Qian

(10) Patent No.: US 11,746,085 B2
(45) Date of Patent: Sep. 5, 2023

(54) TRIPHENYLSULFONIUM SALT COMPOUND, AND USES THEREOF

(71) Applicants: Changzhou Tronly Advanced Electronic Materials Co., Ltd., Jiangsu (CN); Changzhou Tronly New Electronic Materials Co., Ltd., Jiangsu (CN)

(72) Inventor: Xiaochun Qian, Jiangsu (CN)

(73) Assignees: Changzhou Tronly Advanced Electronic Materials Co., Ltd., Jiangsu (CN); Changzhou Tronly New Electronics Materials Co., Ltd., Jiangsu (CN)

( * ) Notice: Subject to any disclaimer, the term of this patent is extended or adjusted under 35 U.S.C. 154(b) by 310 days.

(21) Appl. No.: 17/284,274

(22) PCT Filed: Sep. 27, 2019

(86) PCT No.: PCT/CN2019/108369
§ 371 (c)(1),
(2) Date: Apr. 9, 2021

(87) PCT Pub. No.: WO2020/073822
PCT Pub. Date: Apr. 16, 2020

(65) Prior Publication Data
US 2021/0387948 A1    Dec. 16, 2021

(30) Foreign Application Priority Data

Oct. 9, 2018  (CN) .......................... 201811171951.X
Oct. 9, 2018  (CN) .......................... 201811172185.9

(51) Int. Cl.
C07C 381/12    (2006.01)
C07D 209/88    (2006.01)
C07D 307/91    (2006.01)
C07D 333/76    (2006.01)
G03F 7/004     (2006.01)

(52) U.S. Cl.
CPC .......... *C07C 381/12* (2013.01); *C07D 209/88* (2013.01); *C07D 307/91* (2013.01); *C07D 333/76* (2013.01); *G03F 7/004* (2013.01)

(58) Field of Classification Search
CPC .................................................. C07C 381/12
See application file for complete search history.

(56) References Cited

U.S. PATENT DOCUMENTS

| | | | | |
|---|---|---|---|---|
| 11,281,099 B2* | 3/2022 | Yamazaki | ............. | G03F 7/0392 |
| 11,435,665 B2* | 9/2022 | Hatakeyama | ........ | C07D 307/93 |
| 11,467,490 B2* | 10/2022 | Masuyama | ........... | C07C 309/06 |
| 2002/0006582 A1 | 1/2002 | Inoue et al. | | |
| 2004/0030158 A1 | 2/2004 | Date et al. | | |
| 2004/0033434 A1 | 2/2004 | Fukasawa et al. | | |
| 2006/0178449 A1 | 8/2006 | Tsuchimura et al. | | |
| 2011/0112306 A1 | 5/2011 | Fujiwara et al. | | |
| 2011/0152540 A1 | 6/2011 | Nakayashiki et al. | | |
| 2011/0189609 A1* | 8/2011 | Kawabata | ............. | C07D 333/46 430/296 |
| 2013/0035503 A1 | 2/2013 | Cho et al. | | |
| 2014/0199630 A1 | 7/2014 | Fukushima et al. | | |
| 2014/0357896 A1 | 12/2014 | Furuta et al. | | |
| 2016/0376233 A1* | 12/2016 | Yamazaki | ............. | G03F 7/2059 430/270.1 |
| 2023/0094313 A1* | 3/2023 | Aqad | .................... | C07C 381/12 430/270.1 |

FOREIGN PATENT DOCUMENTS

| CN | 1508624 A | 6/2004 |
|---|---|---|
| CN | 104703809 A | 6/2015 |

(Continued)

OTHER PUBLICATIONS

Ignatov, L. Ya. et al. "Activating effect of the diphenylsulfoniumgroup in the nucleophilic substitution of chlorine in the benzene ring." Doklady Akademii Nauk SSSR. 1976. vol. 231, (4). pp. 874-877.
Office Action Issued in Japanese Patent Application No. 2021-519803. dated Jun. 7, 2022.
Asakura et al "PAG Study in EUV Lithography" Journal of Photopolymer Science and Technology vol. 22, pp. 89-95, Jan. 1, 2009.

(Continued)

*Primary Examiner* — Amanda C. Walke
(74) *Attorney, Agent, or Firm* — Cesari & McKenna, LLP

(57) ABSTRACT

The present invention discloses a triphenylsulfonium salt compound as shown in the general formula (I), wherein $R_1$ represents an electron-withdrawing group and $R_2$ represents an amplification group. Said compound shows significantly enhanced solubility and photosensitivity compared with unsubstituted triphenylsulfonium salts, and has significantly advantageous performance compared with prior art improved substitutes.

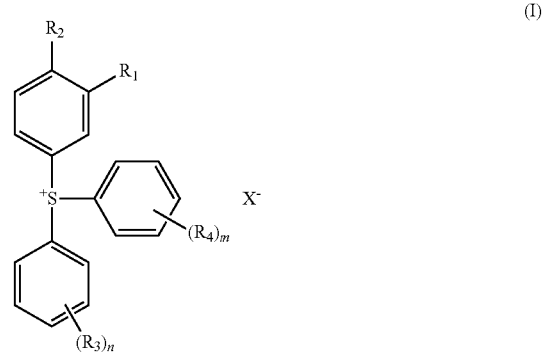

(I)

20 Claims, No Drawings

(56) References Cited

FOREIGN PATENT DOCUMENTS

| | | |
|---|---|---|
| CN | 105278249 A | 1/2016 |
| CN | 107698477 A | 2/2018 |
| CN | 108530421 A | 9/2018 |
| EP | 0704433 A1 | 4/1996 |
| EP | 1350789 A1 | 10/2003 |
| EP | 1431032 A1 | 6/2004 |
| EP | 1557413 A1 | 7/2005 |
| EP | 1676835 A1 | 7/2006 |
| EP | 2042487 A2 | 4/2009 |
| EP | 2264007 A1 | 12/2010 |
| EP | 2905144 A1 | 8/2015 |
| JP | H08245566 A | 9/1996 |
| JP | H08311018 A | 11/1996 |
| JP | H10330353 A | 12/1998 |
| JP | 2004271843 A | 9/2004 |
| JP | 2005062800 A | 3/2005 |
| JP | 2006241435 A | 9/2006 |
| JP | 2009084219 A | 4/2009 |
| JP | 2011/063657 A | 3/2011 |
| JP | 2011140559 A | 7/2011 |
| JP | 2019038764 A | 3/2019 |
| JP | 2019207404 A | 12/2019 |
| WO | WO-2010/046240 A1 | 4/2010 |
| WO | WO-2011/104127 A1 | 9/2011 |
| WO | WO-2014050435 A1 | 4/2014 |
| WO | WO-2015151759 A1 * | 10/2015 ............... G03F 1/22 |
| WO | WO-2020/073822 A1 | 4/2020 |

OTHER PUBLICATIONS

Extended Search Report issued in European Patent Application No. 19 871 797.7 dated Oct. 10, 2022.

Office Action dated Feb. 19, 2021 for Chinese Patent Application No. 201811172185.9.

* cited by examiner

TRIPHENYLSULFONIUM SALT COMPOUND, AND USES THEREOF

CROSS REFERENCE TO RELATED APPLICATIONS

This application is the National Stage of International Application No. PCT/CN2019/108369, filed on Sep. 27, 2019, which claims priority to Chinese Application No. 201811172185.9, filed on Oct. 9, 2018, and Chinese Application No. 201811171951.X, filed on Oct. 9, 2018. The contents of these applications are hereby incorporated by reference in their entirety.

TECHNICAL FIELD

The present invention belongs to the technical field of functional organic compound, in particular relates to a novel triphenylsulfonium salt compound and uses thereof.

BACKGROUND

Compared with free radical type system, the cationic photocuring system has advantages such as less inhibition by oxygen, less volume shrinkage during curing, and broader selection for the types of resins, and is widely used in the manufacture of electronic parts and semiconductor elements. The triphenylsulfonium salt has high photosensitive activity against exposure light source such as KrF or ArF excimer laser, and is generally used as photo-acid generator/photoinitiator for chemical amplification resist, for mass-production of semiconductor elements. However, the cationic structure of triphenylsulfonium salt is symmetrical and has high crystallinity. It has poor solubility in photo-curable system monomers and conventional organic solvents, resulting in limited addition amounts, and it is prone to have problems such as non-homogeneous dispersion in the composition and precipitation during use.

To improve solubility, JP2005091976A and JP2002193925A introduce the substituent such as alkyl and fluoroalkyl at the para-position of the benzene ring group. WO2005037778A introduces alkyl at the meta-position of the benzene ring group, and compared with the unsubstituted one, such compounds have improved solubility in solvents, but greatly reduced photosensitive activity. TW201444790A introduces an electron-withdrawing group at the meta-position of the benzene ring group, and compared with the unsubstituted one, such compounds can maintain the photosensitive activity at the same level while improving the solubility.

There are continued technical and market demands for optimizing the structure of triphenylsulfonium salt to obtain alternatives having better application performances.

SUMMARY

An main purpose of the present invention is to provide a triphenylsulfonium salt compound and uses thereof, to solve the problem that the triphenylsulfonium salt structure in the prior art cannot have both high solubility and high photosensitive.

To meet the demands in the application market, the present invention aims to provide a novel triphenylsulfonium salt compound on the basis of the prior art through structure modifications, which has excellent solubility and photosensitive activity, and can serve as superior alternatives for resist acid generator and photoinitiator for cationic polymerization.

According to one aspect of the present invention, a triphenylsulfonium salt compound is provided, having a structure represented by the following general formula (I) or general formula (III):

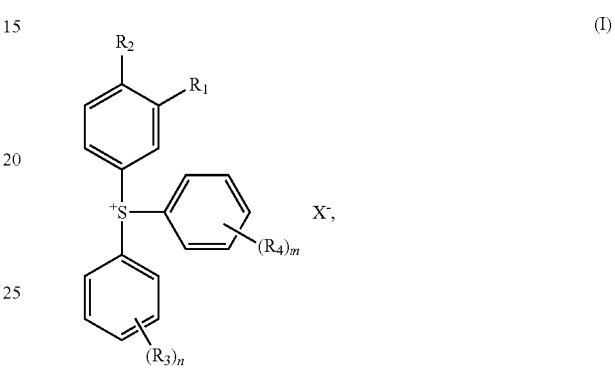

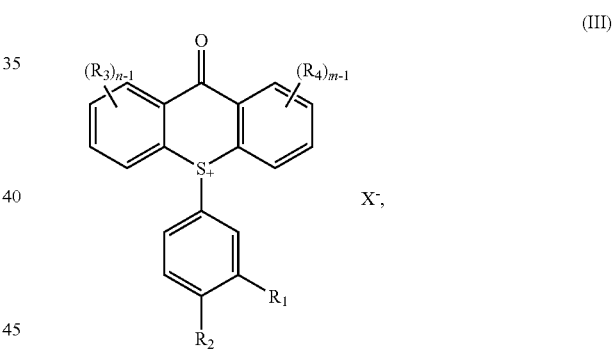

wherein, $R_1$ represents an electron-withdrawing group; $R_2$ represents an amplification group;

each $R_3$ independently represents any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, —$CH_2$— in the groups representing $R_3$ may be replaced with —O— or —S—, and $R_3$ groups may be connected with each other to form a ring; each $R_4$ and $R_5$ independently represent any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, —$CH_2$— in the groups representing $R_4$ and $R_5$ may be replaced with —O—, —S—, or —CH=CH—, and $R_4$ groups may be connected with each other to form a ring; n and m each independently represent an integer of 0 to 5; and $X^-$ represents a non-nucleophilic anion.

According to another aspect of the present invention, the provided triphenylsulfonium salt compound can also be bis-triphenylsulfonium salt compound, having a structure represented by general formula (II):

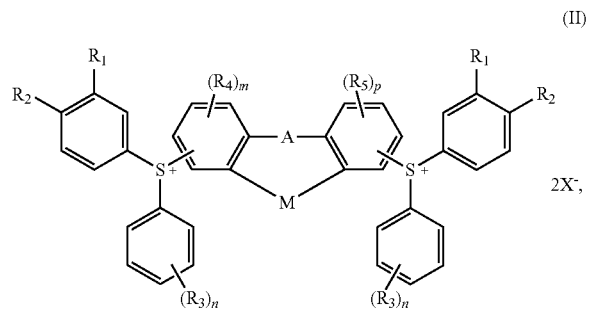

(II)

wherein, $R_1$ represents an electron-withdrawing group; $R_2$ represents an amplification group; each $R_3$ independently represents any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups representing $R_3$ may be interrupted by —O— or —S—, and $R_3$ groups may be connected with each other to form a ring; n represents an integer of 0 to 5; each $R_4$ independently represents any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups representing $R_4$ may be interrupted by —O— or —S—, and $R_4$ groups may be connected with each other to form a ring; m represents an integer of 0 to 4; each $R_5$ independently represents any of hydrogen, halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups representing $R_5$ may be interrupted by —O— or —S—, and $R_5$ groups may be connected with each other to form a ring; p represents an integer of 0 to 4; A and M each independently represent a linking group; $X^-$ represents a non-nucleophilic anion.

According to yet another aspect of the present invention, the use of each above-mentioned triphenylsulfonium salt compound as a resist acid generator and/or a photoinitiator for cationic polymerization is provided.

According to yet another aspect of the present invention, a photosensitive composition comprising any of above-mentioned triphenylsulfonium salt compounds is provided.

According to yet another aspect of the present invention, the use of the above-mentioned photosensitive composition in the manufacture of lithographic and relief printing plates, printing substrates, photoresist, photo-curable printing inks, paints, and adhesives is provided.

Without being limited to any known theory, the uses show that, by configuring an electron-withdrawing group and an amplification group at the meta-position and para-position of the benzene ring group in the triphenylsulfonium salt respectively, it can have significantly improved solubility and photosensitive activity over the unsubstituted triphenylsulfonium salt, and also have significant performance advantages compared to the existing improved alternatives described in the background.

DESCRIPTION OF EMBODIMENTS

It should be noted that, in the case of no conflict, the embodiments in the subject application as well as the features therein can be combined with each other. The present invention will be described in detail below with reference to the embodiments.

The existing literatures show that, the introduction of substituent at the para-position of the benzene ring group is beneficial to improve the solubility of the triphenylsulfonium salt, but has an adverse effect on the photosensitive activity. However, the present applicant has discovered that, when the substituent at the para-position selected from a specific range is combined with an electron-withdrawing group at the meta-position, the solubility and photosensitive activity can be balanced.

In a typical embodiment of the present application, a triphenylsulfonium salt compound having a structure represented by the following general formula (I) is provided:

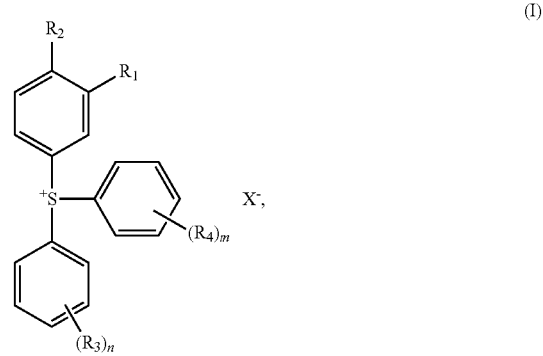

(I)

wherein, $R_1$ represents an electron-withdrawing group; $R_2$ represents an amplification group; each $R_3$ independently represents any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, —$CH_2$— in the groups representing $R_3$ may be replaced with —O— or —S—, and $R_3$ groups may be connected with each other to form a ring; each $R_4$ and $R_5$ independently represent any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, —$CH_2$— in the groups representing $R_4$ and $R_5$ may be replaced with —O—, —S—, or —CH=CH—, and $R_4$ groups may be connected with each other to form a ring; n and m each independently represent an integer of 0 to 5; $X^-$ represents a non-nucleophilic anion.

The application shows that, by configuring an electron-withdrawing group and an amplification group at the meta-position and para-position of the benzene ring group in the triphenylsulfonium salt respectively, it can have significantly improved solubility and photosensitive activity over the unsubstituted triphenylsulfonium salt, and also have significant performance advantages compared to the existing improved alternatives described in the background.

Each variable group in the structure of general formula (I) is illustrated below in more details.

It should be noted that, in the description of this application, $C_1$-$C_x$ includes the carbon numbers with all integer values between 1 and x in addition to 1 and x. For example, $C_1$-$C_8$ alkyl includes all of $C_1$, $C_2$, $C_3$, $C_4$, $C_5$, $C_6$, $C_7$, and $C_8$ linear or branched alkyl groups. Due to space limitations, the descriptions have not been illustrated one by one, while the meanings are definite and unambiguously determined to those skilled in the art. It should be understood that each numeral value therein can be used as the basis for further modification/limitation.

Variable Groups (1) $R_1$ Electron-Withdrawing Group

It is believed that the introduction of electron-withdrawing group at the meta-position of the benzene ring can effectively improve the solubility of sulfonium salt without negative impacts on the photosensitive activity.

As a suitable electron-withdrawing group $R_1$, halogen, cyano, nitro, alkoxy, haloalkyl, acyl, acyloxy, and sulfonyl can be exemplified.

The halogen can be fluorine, chlorine, bromine, or iodine. From the view of cost and environmental performance, fluorine is preferred.

The alkoxy can be $C_1$-$C_8$ linear or branched alkoxy, preferably $C_1$-$C_4$ linear or branched alkoxy, such as methoxy, ethoxy, propoxy, etc.

The haloalkyl refers to alkyl in which at least one hydrogen atoms are replaced with halogen. The alkyl can be $C_1$-$C_8$ linear alkyl such as methyl, ethyl, n-propyl, n-butyl, n-pentyl, and n-hexyl, etc, or $C_3$-$C_8$ branched alkyl such as isopropyl, isobutyl, sec-butyl, tert-butyl, etc, or $C_3$-$C_8$ cycloalkyl such as cyclopropyl, cyclobutyl, cyclopentyl, cyclohexyl, etc. When the haloalkyl is selected from fluorine-substituted alkyl, it is beneficial for the photosensitive activity of the compound, and $C_1$-$C_a$ perfluoroalkyl is more preferred.

The acyl can have a structure represented by

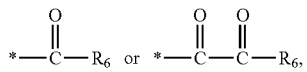

wherein $R_6$ represents hydrogen, halogen, substituted or unsubstituted alkyl, substituted or unsubstituted aryl. Preferably, $R_6$ represents hydrogen, fluorine, chlorine, $C_1$-$C_7$ linear or branched alkyl, or $C_1$-$C_7$ linear or branched fluoroalkyl (more preferably, $C_1$-$C_7$ linear or branched perfluoroalkyl).

The acyl in acyloxy has the same meaning as the acyl described in the above paragraph.

The sulfonyl can be methanesulfonyl, difluoromethanesulfonyl, trifluoromethanesulfonyl, benzenesulfonyl, toluenesulfonyl, etc.

In the general formula (I) of the present invention, the electron-withdrawing group $R_1$ is preferably halogen, cyano, nitro, haloalkyl, or acyl, in particular those specific radicals listed in each above-mentioned group.

(2) $R_2$ Amplification Group

The so-called amplification group refers to the group having an amplification effect on the solubility and/or photosensitive activity of the compound.

It is reported in the existing literatures that, the introduction of substituent at the para-position of the benzene ring group in the triphenylsulfonium salt can improve solubility, but significantly reduce the photosensitive activity. Unexpectedly, in the case that the electron-withdrawing group $R_1$ is existed at the meta-position of the benzene ring group, the introduction of amplification group $R_2$ at the para-position can have an amplification effect on the solubility and/or photosensitive activity of the compound, and would not negatively impact other performances while further improving this performance.

As a group capable of exhibiting an amplification effect, $R_2$ is selected from halogen, substituted or unsubstituted alkyl, substituted or unsubstituted alkoxy, and substituted or unsubstituted aralkyl.

The halogen is preferably fluorine.

The alkyl is preferably unsubstituted alkyl, and can be $C_1$-$C_8$ linear alkyl such as methyl, ethyl, n-propyl, n-butyl, n-pentyl, n-hexyl, etc, or $C_3$-$C_8$ branched alkyl such as isopropyl, isobutyl, sec-butyl, tert-butyl, etc. More preferably, the alkyl as an amplification group is $C_1$-$C_4$ linear or branched alkyl, including methyl, ethyl, n-propyl, isopropyl, n-butyl, or isobutyl.

The alkoxy is preferably unsubstituted, wherein the alkyl has the same meaning as the alkyl described in the above paragraph.

The aralkyl is aryl-terminated alkyl, and from the view of amplification effect, preferably phenyl-terminated $C_1$-$C_8$ alkyl, more preferably phenyl-terminated $C_1$-$C_4$ linear alkyl, including benzyl, phenylethyl, phenylpropyl, or phenylbutyl.

Without being limited to existing known theory, the combination of amplification group and electron-withdrawing group has a synergistic effect on the microscopic electronic structure of the triphenylsulfonium salt, improving the performance of the compound. More specifically, by using the above-mentioned amplification group, the present invention can further improve the solubility of the triphenylsulfonium salt without any negative impacts on the photosensitive activity, and even a part of compounds show relatively better photosensitive activities.

(3) $R_3$ Substituent

The structure of general formula (I) may optionally contain $R_3$ substituent(s), provided that it does not negatively impact the photocuring application performance of the compound.

Under this prerequisite, from the view of providing more alternatives of the same kind, $R_3$ each independently represent hydrogen, halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, —$CH_2$— in the groups may be replaced with —O— or —S—, and $R_3$ groups may be connected with each other to form a ring, wherein the feature "$R_3$ groups may be connected with each other to form a ring" preferably means that two adjacent $R_3$ together with the benzene ring form a ring.

n represents the number of $R_3$ groups, and can be an integer of 0 to 5.

On the basis of the basic theory in the organic field, those skilled in the art can know that the presence of $R_3$ substituent can affect the conjugate structure of the benzene ring where it exists as well as the overall structural characteristics of triphenylsulfonium. Without being limited to any theory, the result from this influence is usually unpredictable, highly depending upon the final presentation of the test.

Preferably, n is 0. In this case, side reactions which may occur in the subsequent photocuring process caused by the substituent, or unknown negative impacts on the effect, can be avoided.

More preferably, n is 2, and two $R_3$ respectively represent $R_1$ and $R_2$, which are symmetrical with $R_1$ and $R_2$ of the uppermost benzene ring on the upper and lower sides. That is, the triphenylsulfonium salt of the present invention has a structure represented by the following general formula (IV):

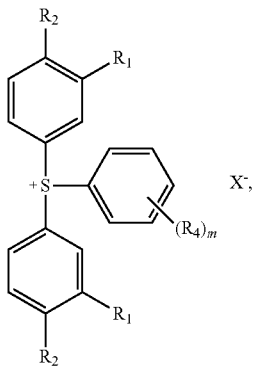

(IV)

wherein, $R_1$ and $R_2$ have the same meanings as described above, and the electron-withdrawing group $R_1$ is preferably halogen, cyano, nitro, haloalkyl, acyl, $R_2$ is preferably fluorine, methyl, ethyl, n-propyl, n-butyl, n-pentyl, n-hexyl, isopropyl, isobutyl, sec-butyl, tert-butyl, methoxy, ethoxy, n-propoxy, n-butoxy, n-pentyloxy, n-hexyloxy, isopropoxy, isobutoxy, sec-butoxy, tert-butoxy, benzyl, phenethyl, phenylpropyl, or phenylbutyl. m represents 0, 1, or 2, more preferably 0 or 1. When m is 1, $R_4$ is preferably located at the para-position of the benzene ring group.

Unexpectedly, in the case of having the same anion moiety, when the triphenylsulfonium salt contains symmetrical electron-withdrawing groups and amplification groups as shown in the above structures in the upper and lower two benzene ring groups. Compared with the improved triphenylsulfonium salt in the prior art, this compound exhibits significantly further improved solubility and photosensitive activity.

(4) $R_4$ Substituent

The structure of general formula (I) may optionally contain $R_4$ substituent(s), provided that it does not negatively impact the photocuring application performance of the compound.

Under this prerequisite, from the view of providing more alternatives of the same kind, $R_4$ each independently represents hydrogen, halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, —$CH_2$— in the groups may be replaced with —O—, —S—, or —CH=CH—, and $R_4$ groups may be connected with each other to form a ring, wherein "$R_4$ groups may be connected with each other to form a ring" preferably means that two adjacent $R_4$s together with the benzene ring form a ring.

The halogen can be fluorine, chlorine, bromine, or iodine. From the view of cost and environmental performance, fluorine is preferred.

The acyl can be selected from: $C_2$-$C_8$ aliphatic acyl, such as acetyl, propionyl, butyryl, valeryl, isovaleryl, caproyl, caprylyl, and heptanoyl; $C_7$-$C_{12}$ aromatic acyl, such as benzoyl, methylbenzoyl, trimethylbenzoyl, α-hydrocinnamoyl, and naphthoyl.

The acyl in acyloxy can have the same meaning as described in the above paragraph.

The sulfonyl can be methanesulfonyl, difluoromethanesulfonyl, trifluoromethanesulfonyl, benzenesulfonyl, toluenesulfonyl, etc.

The alkyl can be substituted or unsubstituted. The alkyl can be selected from $C_1$-$C_8$ linear, $C_3$-$C_8$ branched, or $C_3$-$C_8$ cyclic alkyl, for example: methyl, ethyl, n-propyl, isopropyl, n-butyl, isobutyl, sec-butyl, tert-butyl, n-pentyl, isopentyl, sec-pentyl, tert-pentyl, neopentyl, n-hexyl, isohexyl, 3-methylpentyl, 2-methylpentyl, 1,2-dimethylbutyl, cyclopropyl, cyclopentyl, cyclohexyl, etc. Preferably, the alkyl is selected from $C_1$-$C_4$ linear or branched alkyl, or $C_3$-$C_6$ cyclic alkyl. The substituent in substituted alkyl includes (but not limited to): halogen (fluorine, chlorine, bromine, iodine), amino, hydroxy, etc.

The alkoxy can be substituted or unsubstituted, wherein the alkyl and substituent have the same meanings as described in the above paragraph.

The aryl can be substituted or unsubstituted. The aryl can be phenyl, naphthyl, anthryl, pyrenyl, etc. As the substituent, it can be: $C_1$-$C_4$ alkyl (such as methyl, ethyl, propyl, butyl, etc.), halogen (such as fluorine, chlorine, bromine, and iodine), $C_1$-$C_3$ alkoxy (such as methoxy, ethoxy, and propoxy), acyl, sulfonyl, hydroxy, amino, nitro, phenyl, etc.

The aralkyl is aryl-terminated alkyl, and can be substituted or unsubstituted. Among other, the aryl moiety and substituent can have the same meaning as described in the above paragraph. As the alkyl moiety therein, it is preferably $C_1$-$C_6$ alkylene, including methylene, ethylene, etc. Particularly preferably, the aralkyl is benzyl, phenethyl, or phenylpropyl; optionally, at least one hydrogen on the phenyl is replaced with the substituent as shown in the above paragraph.

m represents the number of $R_4$ groups, and can be an integer of 0 to 5. Preferably, m represents 0, 1, or 2, more preferably 0 or 1. When m is 1, $R_4$ is preferably located at the para-position of the benzene ring group.

(5) Non-Nucleophilic Anion $X^-$ represents a non-nucleophilic anion, including (but not limited to): $M^-$, $ClO_4^-$, $CN^-$, $HSO_4^-$, $NO_3^-$, $CF_3COO^-$, $(BM_4)^-$, $(SbM_6)^-$, $(AsM_6)^-$, $(PM_6)^-$, $Al[OC(CF_3)_3]_4^-$, $R_7SO_3^-$, $(R_7SO_2)_3C^-$, $(R_7SO_2)_2N^-$, $B(C_6M_5)_4^-$, $Ga(C_6M_5)_4^-$, or $[(Rf)_bPF_{6-b}]^-$.

M represents halogen, such as fluorine, chlorine, bromine, and iodine, preferably fluorine.

$R_7$ represents $C_1$-$C_{20}$ alkyl, $C_1$-$C_{20}$ perfluoroalkyl, or $C_6$-$C_{20}$ aryl or substituted aryl, and the alkyl and perfluoroalkyl can be any of linear, branched, or cyclic ones.

Rf represents alkyl in which ≥80% of hydrogen atoms are replaced with fluorine atoms, and the alkyl can exemplified as: linear alkyl (such as methyl, ethyl, propyl, butyl, pentyl, hexyl, octyl, etc.), branched alkyl (such as isopropyl, isobutyl, sec-butyl, tert-butyl, etc.), cycloalkyl (such as cyclopropyl, cyclobutyl, cyclopentyl, cyclohexyl, etc.). In Rf, on the basis of the mole number of original hydrogen atoms in the alkyl, the proportion of the replacement by fluorine atom is preferably 80% or above, preferably 90% or above, more preferably 100%. If the proportion of the replacement by fluorine atom is within these ranges, the photosensitivity of the compound becomes better. Further, Rf can be exemplified as: $CF_3^-$, $CF_3CF_2^-$, $(CF_3)_2CF^-$, $CF_3CF_2CF_2^-$, $CF_3CF_2CF_2CF_2^-$, $(CF_3)_2CFCF_2^-$, $CF_3CF_2(CF_3)CF^-$, and $(CF_3)_3C^-$. b represents an integer of 1 to 5, and Rf groups (with the number b) may be identical to or different from each other.

The anion represented by $M^-$ can be exemplified as: $Cl^-$, $Br^-$, and $F^-$.

The anion represented by $(BM_4)^-$, $(SbM_6)^-$, $(AsM_6)^-$, and $(PM_6)^-$ can be exemplified as: $BF_4^-$, $SbF_6^-$, $AsF_6^-$, and $PF^-$.

The anion represented by $R_7SO_3^-$ can be exemplified as: $CF_3SO_3^-$, $C_2F_5SO_3^-$, $C_3F_7SO_3^-$, $C_4F_9SO_3^-$, $C_6F_5SO_3^-$, $C_3F_7SO_3^-$, p-toluenesulfonate anion, benzenesulfonate anion, camphorsulfonate anion, methanesulfonate anion, ethanesulfonate anion, propanesulfonate anion, and butanesulfonate anion.

The anion represented by $(R_7SO_2)_3C^-$ can be exemplified as: $(CF_3SO_2)_3C^-$, $(C_2F_5SO_2)_3C^-$, $(C_3F_7SO_2)_3C^-$, and $(C_4F_9SO_2)_3C^-$.

The anion represented by $(R_7SO_2)_2N^-$ can be exemplified as: $(CF_3SO_2)_2N^-$, $(C_2F_5SO_2)_2N^-$, $(C_3F_7SO_2)_2N^-$, and $(C_4F_9SO_2)_2N^-$.

The anion represented by $B(C_6M_5)_4^-$ and $Ga(C_6M_5)_4^-$ can be exemplified as: $B(C_6F_5)_4^-$ and $Ga(C_6F_5)_4^-$.

The anion represented by $[(Rf)_bPF_{6-b}]^-$ can be exemplified as: $(CF_3CF_2)_2PF_4^-$, $(CF_3CF_2)_3PF_3^-$, $[(CF_3)_2CF]_2PF_4^-$, $[(CF_3)_2CF]_3PF_3^-$, $(CF_3CF_2CF_2)_2PF_4^-$, $(CF_3CF_2CF_2)_3PF_3^-$, $[(CF_3)_2CFCF_2]_2PF_4^-$, $[(CF_3)_2CFCF_2]_3PF_3^-$, $(CF_3CF_2CF_2CF_2)_2PF_4^-$, $(CF_3CF_2CF_2CF_2)_3PF_3^-$, etc.

Preparation Method

The method for preparing the triphenylsulfonium salt compound of the present invention is not particularly limited, and well-known organic synthesis processes can be employed. For example, reference may be made to the preparation method described in the patent literature CN1871212A (which is hereby incorporated by reference in its entirety). A commercially available diaryl sulfoxide is reacted with an aryl compound through a sulfonium reaction to obtain a sulfonium salt, followed by a salt exchange reaction as needed to introduce an anion, thereby obtaining the triphenylsulfonium salt compound of the present invention.

Use

The triphenylsulfonium salt compound of the present invention has a characteristic of releasing Lewis acid through irradiation by energy rays, and can be used as a resist acid generator and a photoinitiator for cationic polymerization.

As suitable energy rays, those in ultraviolet-visible region obtained from low-pressure, medium-pressure, high-pressure or ultrahigh-pressure mercury lamps, metal halide lamps, LED lamps, xenon lamps, carbon arc lamps, fluorescent lamps, semiconductor solid-state lasers, argon lasers, He—Cd lasers, KrF excimer lasers, ArF excimer lasers, or $F_2$ lasers or the like can be used. The high-energy rays such as electron beams or X-rays or the like can also be used.

The triphenylsulfonium salt compound of the present invention is mixed with a photosensitive active monomer (such as a cationic polymerizable compound) to form a photosensitive composition, which can be applied in the manufacture of lithographic and relief printing plates, printing substrates as well as photoresists for IC and LSI, photo-curable printing inks, paints, adhesives, and other fields.

The triphenylsulfonium salt compound represented by the above general formula (I) in the present invention has excellent solubility, relatively high light generation efficiency and photosensitive activity, and has great application value in the market.

Extension

As an extension of the structure of the above-mentioned triphenylsulfonium salt compound in the present invention, the present invention also provides a thioxanthone sulfonium salt, having a structure represented by the following general formula (III):

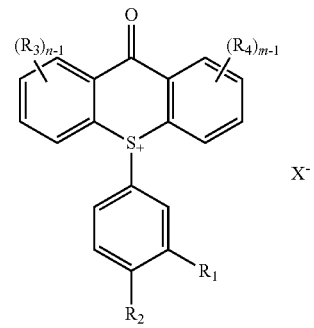

wherein $R_1$, $R_2$, $R_3$, $R_4$, and $X^-$ have the same meanings as described above, and n and in each independently represent an integer of 1 to 5.

The above-mentioned thioxanthone sulfonium salt can be deemed as a structure of general formula (I) formed after connecting one $R_3$ with one $R_4$ to constitute a ketone group, and can also be considered to be capable of achieving similar beneficial effects to the triphenylsulfonium salt compound represented by general formula (I).

The preparation method for this compound can be synthesized by reference to the process described in the patent literature WO2003072567 which is hereby incorporated by reference in its entirety.

Representatively, it can be synthesized by the following process:

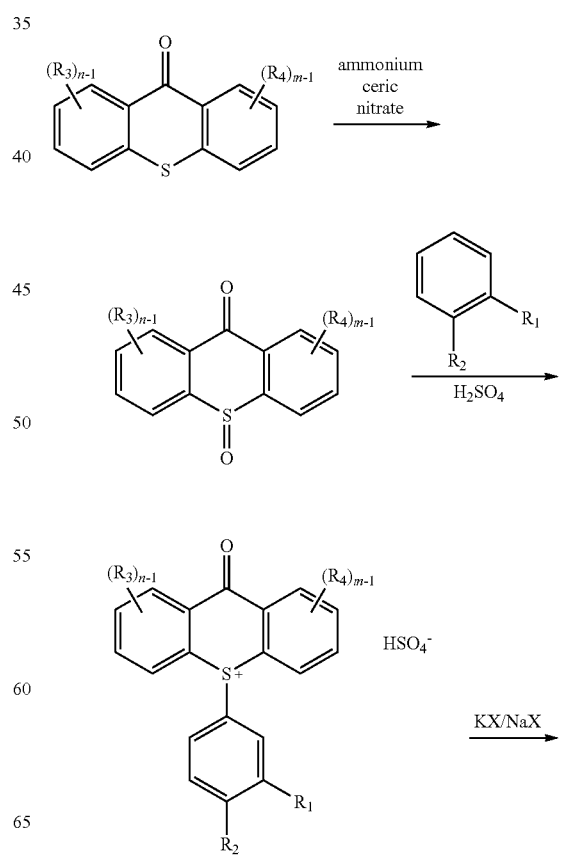

-continued

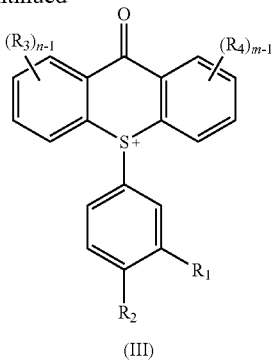

(III)

In yet another typical embodiment of the subject application, another triphenylsulfonium salt compound is provided, which is a bis-triphenylsulfonium salt compound having a structure represented by the following general formula (II):

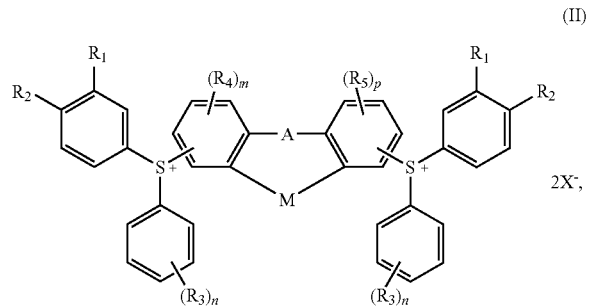

wherein, $R_1$ represents an electron-withdrawing group; $R_2$ represents an amplification group; each $R_3$ independently represents any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups representing $R_3$ may be interrupted by —O— or —S—, and $R_3$ groups may be connected with each other to form a ring; n represents an integer of 0 to 5; each $R_4$ independently represents any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups representing $R_4$ may be interrupted by —O— or —S—, and $R_4$ groups may be connected with each other to form a ring; m represents an integer of 0 to 4; each $R_5$ independently represents any of hydrogen, halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups representing $R_5$ may be interrupted by —O— or —S—, and $R_5$ groups may be connected with each other to form a ring; p represents an integer of 0 to 4; A and M each independently represent a linking group; $X^-$ represents a non-nucleophilic anion.

The use shows that, by configuring an electron-withdrawing group and an amplification group at the meta-position and para-position of the benzene ring group in the bis-triphenylsulfonium salt respectively, it can have significantly improved solubility and photosensitive activity over the unsubstituted triphenylsulfonium salt, and also have significant performance advantages compared to the existing improved alternatives described in the background.

Each variable group in the structure of general formula (II) is illustrated below in more details.

It should be noted that, in the description of this application, $C_1$-$C_x$ includes the carbon numbers with all integer values between 1 and x in addition to 1 and x. For example, $C_1$-$C_8$ alkyl includes all of $C_1$, $C_2$, $C_3$, $C_4$, $C_5$, $C_6$, $C_7$, and $C_8$ linear or branched alkyl groups. Due to space limitations, the descriptions have not been illustrated one by one, while the meanings are definite and unambiguously determined to those skilled in the art. It should be understood that each numeral value therein can be used as the basis for further modification/limitation.

Variable Groups (1) $R_1$ Electron-Withdrawing Group

It is believed that the introduction of electron-withdrawing group at the meta-position of the benzene ring can effectively improve the solubility of the sulfonium salt, without negative impacts on the photosensitive activity.

As a suitable electron-withdrawing group $R_1$, it is selected from halogen, cyano, nitro, haloalkyl, acyl, acyloxy, and sulfonyl.

The halogen can be fluorine, chlorine, bromine, or iodine. From the view of environmental performance, fluorine is preferred.

The haloalkyl refers to alkyl in which at least one hydrogen atoms are replaced with halogen. The alkyl can be $C_1$-$C_8$ linear alkyl such as methyl, ethyl, n-propyl, n-butyl, n-pentyl, and n-hexyl, or $C_3$-$C_8$ branched alkyl such as isopropyl, isobutyl, sec-butyl, tert-butyl, etc, or $C_3$-$C_8$ cycloalkyl such as cyclopropyl, cyclobutyl, cyclopentyl, cyclohexyl, etc. When the haloalkyl is selected from fluorine-substituted alkyl, it is beneficial for the photosensitive activity of the compound, and $C_1$-$C_4$ perfluoroalkyl is more preferred.

The acyl can have a structure represented by

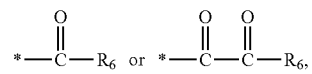

wherein $R_6$ represents hydrogen, halogen, substituted or unsubstituted alkyl, substituted or unsubstituted aryl, substituted or unsubstituted aralkyl. Preferably, $R_6$ represents hydrogen, fluorine, chlorine, $C_1$-$C_7$ linear or branched alkyl, $C_1$-$C_7$ linear or branched haloalkyl (more preferably, $C_1$-$C_7$ linear or branched perfluoroalkyl), $C_6$-$C_{12}$ aryl, or $C_7$-$C_{16}$ aralkyl.

The acyl in acyloxy has the same meaning as the acyl described in the above paragraph.

The sulfonyl can be methanesulfonyl, difluoromethanesulfonyl, trifluoromethanesulfonyl, benzenesulfonyl, toluenesulfonyl, etc.

In the general formula (II) of the present invention, the electron-withdrawing group $R_1$ is preferably halogen, cyano, nitro, or haloalkyl, in particular those preferred groups as mentioned above.

(2) $R_2$ Amplification Group

The so-called amplification group refers to the group having an amplification effect on the solubility and/or photosensitive activity of the compound.

It is reported in the existing literatures that, the introduction of substituent at the para-position of the benzene ring group in the triphenylsulfonium salt can improve solubility, but significantly reduce the photosensitive activity. Unexpectedly, in the case that the electron-withdrawing group $R_1$ is existed at the meta-position of the benzene ring group, the introduction of amplification group $R_2$ at the para-position can have an amplification effect on the solubility and/or photosensitive activity of the compound, and would not negatively impact other performances while further improving this performance.

As a group capable of exhibiting an amplification effect in the present invention, $R_2$ is selected from substituted or unsubstituted alkyl, substituted or unsubstituted alkoxy, and substituted or unsubstituted aralkyl.

The alkyl is preferably unsubstituted alkyl, and can be $C_1$-$C_8$ linear alkyl such as methyl, ethyl, n-propyl, n-butyl, n-pentyl, n-hexyl, etc, or $C_3$-$C_8$ branched alkyl such as isopropyl, isobutyl, sec-butyl, tert-butyl, etc. More preferably, the alkyl as an amplification group is $C_1$-$C_4$ linear or branched alkyl, including methyl, ethyl, n-propyl, isopropyl, n-butyl, or isobutyl.

The alkoxy is preferably unsubstituted, wherein the alkyl has the same meaning as described in the above paragraph.

The aralkyl is aryl-terminated alkyl, and from the view of amplification effect, preferably phenyl-terminated $C_1$-$C_8$ alkyl, more preferably phenyl-terminated $C_1$-$C_4$ linear alkyl, including benzyl, phenylethyl, phenylpropyl, or phenylbutyl. Optionally, at least one hydrogen atoms in the aralkyl are replaced with halogen (in particular fluorine).

The structure of general formula (II) may optionally contain $R_3$ substituent(s), provided that it does not negatively impact the photocuring application performance of the compound.

Under this prerequisite, from the view of providing more alternatives of the same kind, $R_3$ each independently represents hydrogen, halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups may be interrupted by —O— or —S—, and $R_3$ groups may be connected with each other to form a ring.

n represents the number of $R_3$ groups, and can be an integer of 0 to 5.

On the basis of the basic theory in the organic field, those skilled in the art can know that the presence of $R_3$ substituent can affect the conjugate structure of the benzene ring where it exists as well as the overall structural characteristics of bis-triphenylsulfonium. Without being limited to any theory, the result from this influence is usually unpredictable, highly depending upon the final presentation of the test.

Preferably, n is 0. In this case, side reactions which may occur in the subsequent photocuring process caused by the substituent, or unknown negative impacts on the effect, can be avoided.

More preferably, n is 2, and the two $R_3$ on the same benzene ring respectively represent $R_1$ and $R_2$, which are symmetrical with $R_1$ and $R_2$ of the uppermost benzene ring on the upper and lower sides. That is, the bis-triphenylsulfonium salt of the present invention has a structure represented by the following general formula (V):

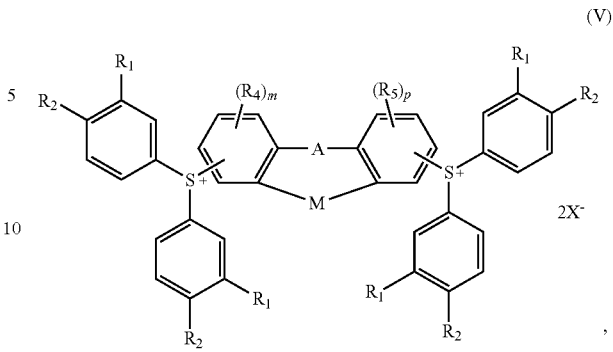

wherein, each substituent has the same meaning as described above.

Unexpectedly, when the bis-triphenylsulfonium salt contains symmetrical electron-withdrawing groups and amplification groups as shown in the above structures in the upper and lower four benzene ring groups. Compared with the improved triphenylsulfonium salt in the prior art, this compound exhibits significantly further improved solubility and photosensitive activity.

(4) $R_4$ Substituent

The structure of general formula (II) may optionally contain $R_4$ substituent(s), provided that it does not negatively impact the photocuring application performance of the compound.

Under this prerequisite, from the view of providing more alternatives of the same kind, $R_4$ each independently represents hydrogen, halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, the carbon-carbon bond in the groups may be interrupted by —O— or —S—, and $R_4$ groups may be connected with each other to form a ring.

The halogen can be fluorine, chlorine, bromine, or iodine. From the view of cost and environmental performance, fluorine is preferred.

The acyl can be selected from: $C_2$-$C_8$ aliphatic acyl, such as acetyl, propionyl, butyryl, valeryl, isovaleryl, caproyl, caprylyl, heptanoyl, etc; $C_7$-$C_{12}$ aromatic acyl, such as benzoyl, methylbenzoyl, trimethylbenzoyl, α-hydrocinnamoyl, naphthoyl, etc.

The acyl in acyloxy can have the same meaning as the acyl described in the above paragraph.

The sulfonyl can be methanesulfonyl, difluoromethanesulfonyl, trifluoromethanesulfonyl, benzenesulfonyl, toluenesulfonyl, etc.

The alkyl can be substituted or unsubstituted. The alkyl can be selected from $C_1$-$C_8$ linear, branched, or cyclic alkyl, for example: methyl, ethyl, n-propyl, isopropyl, n-butyl, isobutyl, sec-butyl, tert-butyl, n-pentyl, isopentyl, sec-pentyl, tert-pentyl, neopentyl, n-hexyl, isohexyl, 3-methylpentyl, 2-methylpentyl, 1, 2-dimethylbutyl, cyclopropyl, cyclopentyl, cyclohexyl, etc. Preferably, the alkyl is selected from $C_1$-$C_4$ linear or branched alkyl, or $C_3$-$C_6$ cyclic alkyl. The substituent in substituted alkyl includes (but not limited to): halogen (fluorine, chlorine, bromine, iodine), amino, hydroxy, etc.

The alkoxy can be substituted or unsubstituted, wherein the alkyl and substituent have the same meanings as described in the above paragraph.

The aryl can be substituted or unsubstituted. The aryl can be phenyl, naphthyl, anthryl, pyrenyl, etc. As the substituent, it can be: $C_1$-$C_4$ alkyl (such as methyl, ethyl, propyl, butyl, etc), halogen (such as fluorine, chlorine, bromine, and iodine), $C_1$-$C_3$ alkoxy (such as methoxy, ethoxy, and propoxy), acyl, sulfonyl, hydroxy, amino, nitro, phenyl, etc.

The aralkyl is aryl-terminated alkyl, and can be substituted or unsubstituted. Among others, the aryl moiety and substituent can have the same meaning as described in the above paragraph. As the alkyl moiety therein, it is preferably $C_1$-$C_6$ alkylene, including methylene, ethylene, etc. Particularly preferably, the aralkyl is benzyl, phenethyl, or phenylpropyl; optionally, at least one hydrogen on the phenyl is replaced with the substituent as shown in the above paragraph.

In the general formula (II) of the present invention, $R_4$ is preferably hydrogen, nitro, cyano, substituted or unsubstituted alkyl, or substituted or unsubstituted alkoxy, in particular those preferred groups as mentioned above.

m represents the number of $R_4$ groups, and can be an integer of 0 to 4. Preferably, m represents 0, 1, or 2, more preferably 0 or 1. When m is 1, $R_4$ is preferably located at the ortho-position on the side of group A.

(5) $R_5$ Substituent

The structure of general formula (II) may optionally contain $R_5$ substituent(s), provided that it does not negatively impact the photocuring application performance of the compound.

In terms of the selection range, $R_5$ may have the same meaning as the above-mentioned $R_4$ substituent. $R_4$ and each $R_5$ together with the phenyl to which each group is connected and group A may form a ring.

p represents the number of $R_5$ groups, and can be an integer of 0 to 4. Preferably, p represents 0, 1, or 2, more preferably 0 or 1. When p is 1, $R_5$ is preferably located at the ortho-position on the side of group A.

(6) Linking Group

As the linking group for two triphenylsulfonium structures, A represents a linking bond i.e., single bond), *O*, *S*, alkylene, or alkenylene, M represents blank,

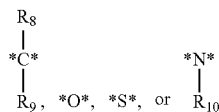

group, wherein * represents the connection position, $R_8$, $R_9$, and $R_{10}$ each independently represent hydrogen, $C_1$-$C_{20}$ linear or branched alkyl, $C_3$-$C_{20}$ cycloalkyl, $C_4$-$C_{20}$ cycloalkylalkyl, or $C_4$-$C_{20}$ alkylcycloalkyl.

Preferably, the alkylene is $C_1$-$C_4$ linear alkylene, and the alkenylene is —CH=CH—.

When M represents blank, it means that two benzene rings are only connected by the linking group A. When M is not blank, it is preferred that A represents a linking bond.

(7) Connection Position

In the bis-triphenylsulfonium salt compound represented by general formula (II) in the present invention, the S atoms on the left and right sides are respectively connected to three benzene rings. On the two benzene rings in the middle, the connection positions of S atoms are preferably at the para-position of group A.

(8) Non-Nucleophilic Anion $X^-$ represents a non-nucleophilic anion, including (but not limited to): $Q^-$, $ClO_4^-$, $CN^-$, $HSO_4^-$, $NO_3^-$, $CF_3COO^-$, $(BQ_4)^-$, $(SbQ_6)^-$, $(AsQ_6)^-$, $(PQ_6)^-$, $Al[OC(CF_3)_3]_4^-$, $R_6SO_3^-$, $(R_6SO_2)_3C^-$, $(R_6SO_2)_2N^-$, $B(C_6Q_5)_4^-$, $Ga(C_6Q_5)_4^-$, or $[(Rf)_bPF_{6-b}]^-$.

Q represents halogen, such as fluorine, chlorine, bromine, and iodine, preferably fluorine.

$R_6$ represents $C_1$-$C_{20}$ alkyl, $C_1$-$C_{20}$ perfluoroalkyl, or $C_6$-$C_{20}$ aryl or substituted aryl, and the alkyl and perfluoroalkyl can be any of linear, branched, or cyclic ones.

Rf represents alkyl in which ≥80% of hydrogen atoms are replaced with fluorine atoms, and the alkyl can exemplified as: linear alkyl (such as methyl, ethyl, propyl, butyl, pentyl, hexyl, octyl, etc.), branched alkyl (such as isopropyl, isobutyl, sec-butyl, tert-butyl, etc,), cycloalkyl (such as cyclopropyl, cyclobutyl, cyclopentyl, cyclohexyl, etc.). In Rf, on the basis of the mole number of original hydrogen atoms in the alkyl, the proportion of the replacement by fluorine atom is preferably 80% or above, preferably 90% or above, more preferably 100%. If the proportion of the replacement by fluorine atom is within these ranges, the photosensitivity of the compound becomes better. Further, Rf can be exemplified as: $CF_3^-$, $CF_3CF_2^-$, $(CF_3)_2CF^-$, $CF_3CF_2CF_2^-$, $CF_3CF_2CF_2CF_2^-$, $(CF_3)_2CFCF_2^-$, $CF_3CF_2(CF_3)CF^-$, and $(CF_3)_3C^-$. b represents an integer of 1 to 5, and Rf groups (with the number b) may be identical to or different from each other.

The anion represented by $Q^-$ can be exemplified as: $Cl^-$, $Br^-$, and $F^-$.

The anion represented by $(BQ_4)^-$, $(SbQ_6)^-$, $(AsQ_6)^-$, and $(PQ_6)^-$ can be exemplified as: $BF_4^-$, $SbF_6^-$, $AsF_6^-$, and $PF^-$.

The anion represented by $R_6SO_3^-$ can be exemplified as: $CF_3SO_3^-$, $C_2F_5SO_3^-$, $C_3F_7SO_3^-$, $C_4F_9SO_3^-$, $C_6F_5SO_3^-$, $C_3F_7SO_3^-$, p-toluenesulfonate anion, benzenesulfonate anion, camphorsulfonate anion, methanesulfonate anion, ethanesulfonate anion, propanesulfonate anion, and butanesulfonate anion.

The anion represented by $(R_6SO_2)_3C^-$ can be exemplified as: $(CF_3SO_2)_3C^-$ $(C_2F_5SO_2)_3C^-$, $(C_3F_7SO_2)_3C^-$, and $(C_4F_9SO_2)_3C^-$.

The anion represented by $(R_6SO_2)_2N^-$ can be exemplified as: $(CF_3SO_2)_2N^-$, $(C_2F_5SO_2)_2N^-$, $(C_3F_7SO_2)_2N^-$, and $(C_4F_9SO_2)_2N^-$.

The anion represented by $B(C_6Q_5)_4^-$ and $Ga(C_6Q_5)_4^-$ can be exemplified as: $B(C_6F_5)_4^-$ and $Ga(C_6F_5)_4^-$.

The anion represented by $[(Rf)_bPF_{6-b}]^-$ can be exemplified as: $(CF_3CF_2)_2PF_4^-$, $(CF_3CF_2)_3PF_3^-$, $[(CF_3)_2CF]_2PF_4^-$, $[(CF_3)_2CF]_3PF_3^-$, $(CF_3CF_2CF_2)_2PF_4^-$, $(CF_3CF_2CF_2)_3PF_3^-$, $[(CF_3)_2CFCF_2]_2PF_4^-$, $[(CF_3)_2CFCF_2]_3PF_3^-$, $(CF_3CF_2CF_2CF_2)_2PF_4^-$, $(CF_3CF_2CF_2CF_2)_3PF_3^-$, etc.

Preparation Method

The method for preparing the bis-triphenylsulfonium salt compound of the present invention is not particularly limited, and well-known organic synthesis processes can be employed. For example, reference may be made to the preparation method described in the patent literature CN1871212A. A diaryl sulfoxide is reacted with a diaryl compound through a sulfonium reaction to obtain a sulfonium salt, followed by a salt exchange reaction as needed to introduce an anion, thereby obtaining the bis-triphenylsulfonium salt compound of the present invention.

Use

The bis-triphenylsulfonium salt compound of the present invention has a characteristic of releasing Lewis acid through irradiation by active energy rays and can act on acid-reactive organic substances for decomposition or polymerization. Thus, it can be used as a photo-acid generator for photoresist or as a cationic polymerization photoinitiator.

As suitable energy rays, those in ultraviolet-visible region obtained from low-pressure, medium-pressure, high-pressure or ultrahigh-pressure mercury lamps, metal halide lamps, LED lamps, xenon lamps, carbon arc lamps, fluorescent lamps, semiconductor solid-state lasers, argon lasers, He—Cd lasers, KrF excimer lasers, ArF excimer lasers, or $F_2$ lasers or the like can be used. The high-energy rays such as electron beams or X-rays or the like can also be used.

The bis-triphenylsulfonium salt compound of the present invention is mixed with a photosensitive active monomer (such as a cationic polymerizable compound) to form a photosensitive composition, which can be applied in the manufacture of lithographic and relief printing plates, printing substrates as well as photoresists for IC and LSI, photo-curable printing inks, paints, adhesives, and other fields.

The bis-triphenylsulfonium salt compound represented by the above general formula (II) in the present invention has excellent solubility, relatively high light generation efficiency and photosensitive activity, and has great application value in the market.

The present invention is further illustrated in details by the following examples; however, these examples should be not interpreted as limiting the protection scope of the present invention.

Regarding the Triphenylsulfonium Salt Compound Having the General Formula (I)

PREPARATION EXAMPLES

Example I-1: Preparation of Sulfonium Salt A-1

(1) Intermediate a1

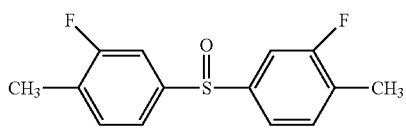

To 500 mL four-necked flask 110.0 g of o-fluorotoluene, 59.5 g of dichlorosulfoxide, and 200 mL of dichloromethane were charged, and cooled in an ice-water bath. The temperature was controlled at approximately 5° C. 66.5 g of aluminium trichloride was added in batches over about 1 hour. It was stirred for additional 2 hours, and the liquid phase was tracked until the reaction was completed. The solution of the product in dichloromethane was poured into 500 g of ice water, and continuously stirred. The dichloromethane layer was separated and washed with water, followed by rotary evaporation of the dichloromethane product solution, to obtain 106 g of light yellow solid, i.e., Intermediate a1 (yield: 79.7%, HPLC purity: 98%).

The structure of the intermediate product was confirmed by H-NMR and MS, and the specific characterization results are as follows:

$^1$H-NMR (CDCl$_3$, 500 MHz): 2.3312 (6H, s), 7.2438-7.3305 (6H, m).

MS (m/Z): 267 (M+H)$^+$.

(2) Intermediate b1

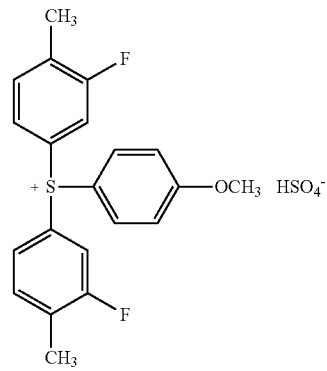

To 500 mL four-necked flask 66.5 g of Intermediate a1 and 200 mL of acetic anhydride were charged, and stirred in an ice-water bath. The temperature was controlled at approximately 0° C. 35 g of concentrated sulfuric acid (mass fraction: 70%) was dropwise added over about 1 hour. After the completion of dropwise addition, to the reaction system 27 g of methoxybenzene was added in batches, and stirred for additional 12 hours. Then 100 mL of deionized ice water was slowly dropwise added. The solution was extracted by benzene 2-3 times, the aqueous layer was separated, and the combined benzene layer was washed with water once. The aqueous layers were combined, to obtain the aqueous solution of Intermediate b1.

(3) Target Product i.e., Compound A-1

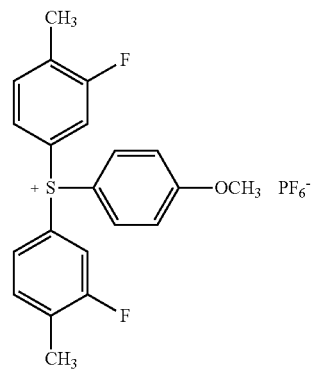

To the above aqueous solution of Intermediate b1, 46 g of KPF$_6$ solid was added for ion exchange, and deionized water was appropriately supplemented under stirring. As the dissolution of KPF$_6$ solid, target product A-1 gradually precipitated, and was filtered and dried, to obtain 77.8 g of white solid (yield: 62.0%, HPLC purity: 99%).

The structure of the target product was confirmed by H-NMR and MS, and the specific characterization results are as follows:

$^1$H-NMR (DCl$_3$, 500 MHz): 2.3312 (6H, s), 3.7345 (3H, s), 6.8038-7.2818 (10H, m).

MS (m/Z): 357 (M)$^+$.

Example I-2: Preparation of Sulfonium Salt A-2

(1) Intermediate a2

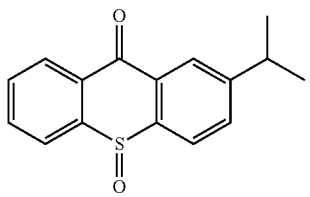 [SMILES: CC(C)c1ccc2c(c1)C(=O)c1ccccc1S2=O]

To 1500 mL four-necked flask 12.7 g of isopropylthioxanthone (ITX) and 800 mL of mixed solution of acetonitrile and water (acetonitrile 75%, water 25%) were charged, and stirred and heated to 35° C. After complete dissolution, 107.9 g of ammonium ceric nitrate was added, and stirred and reacted at room temperature for about 1 hour. The liquid phase was tracked until the reaction was completed. After the completion of reaction, 500 mL of water was added. The mixture was extracted by diethyl ether several times. The organic layer was combined, dried over magnesium sulfate, and rotary evaporated, to obtain 12.5 g of Intermediate a2 (yield: 79.7%, HPLC purity: 98%).

The structure of the intermediate product was confirmed by H-NMR and MS, and the specific characterization results are as follows:

$^1$H-NMR (CDCl$_3$, 500 MHz): 1.2167-2.8743 (7H, m), 7.5912-7.9532 (7H, m).

(2) Intermediate b2

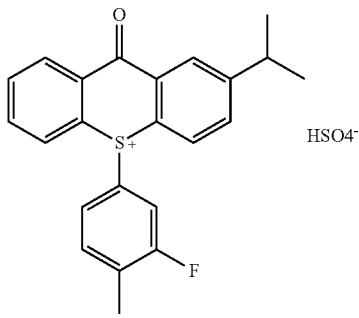

To 500 mL four-necked flask 67.5 g of Intermediate a1 and 200 mL of acetic anhydride were charged, and stirred in an ice-water bath. The temperature was controlled at approximately 0° C. 36 g of concentrated sulfuric acid (mass fraction: 70%) was dropwise added over about 1 hour. After the completion of dropwise addition, to the reaction system 27.5 g of o-fluorotoluene was added in batches, and stirred for additional 12 hours. Then 100 mL of deionized ice water was slowly dropwise added. The solution was extracted by benzene 2-3 times, the aqueous layer was separated, and the combined benzene layer was washed with water once. The aqueous layers were combined, to obtain the aqueous solution of Intermediate b1.

(3) Target Product i.e., Compound A-2

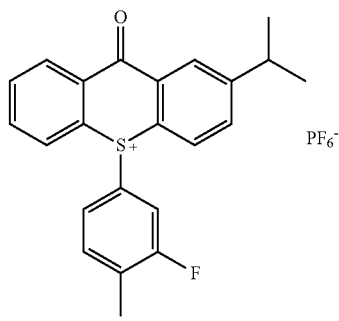

To the above aqueous solution of Intermediate b2 46 g of KPF$_6$ solid was added for ion exchange, and deionized water was appropriately supplemented under stirring. As the dissolution of KPF$_6$ solid, target product A-2 gradually precipitated, and was filtered and dried, to obtain 77.8 g of white solid (yield: 62.0%, HPLC purity: 99%).

The structure of the target product was confirmed by H-NMR and MS, and the specific characterization results are as follows:

$^1$H-NMR (DCl$_3$, 500 MHz): 1.2034-1.2045 (6H, d), 2.3312 (3H, s), 2.8732-2.8745 (1H, m), 6.9908-7.7221 (10H, m).

MS (m/Z): 363 (M)$^+$.

Referring to the preparation method of Example 1, Compounds 3-38 as shown in Table 1 were prepared.

The structures of target products as well as their MS (m/Z) and $^1$H-NMR data were listed in Table 1.

TABLE 1

| Compound | Structure | MS (m/Z) | $^1$H-NMR |
|---|---|---|---|
| A-3 | 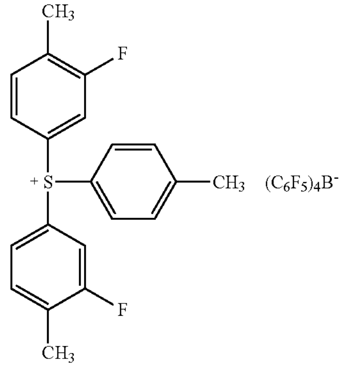 | 341 | 2.3312 (9H, s), 6.8038-7.1218(10H, m) |

TABLE 1-continued
| Compound | Structure | MS (m/Z) | ¹H-NMR |
|---|---|---|---|
| A-4 | 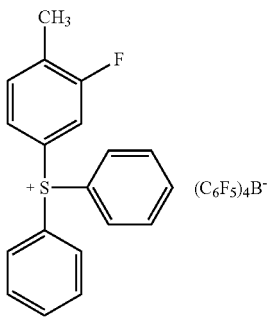 | 295 | 2.3312 (3H, s), 6.8038-7.3410(13H, m) |
| A-5 | 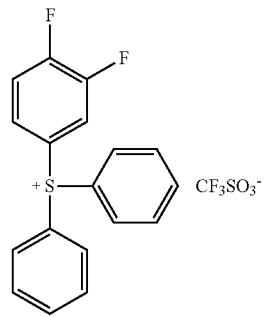 | 299 | 6.9123-7.3410(13H, m) |
| A-6 | 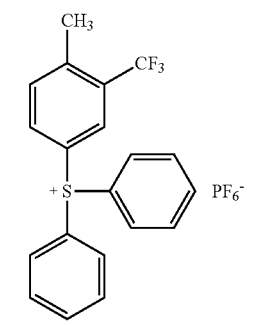 | 345 | 2.2934 (3H, s), 5.2013(1H, d), 7.0943-7.9810(13H, m) |
| A-7 | 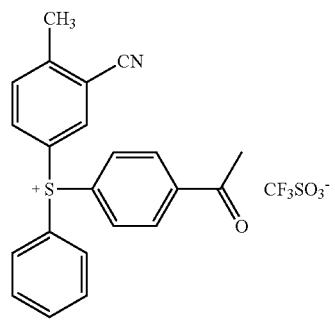 | 344 | 2.4032 (3H, s), 2.5043 (3H, s), 7.2145-7.9600 (12H, m) |

TABLE 1-continued
| Compound | Structure | MS (m/Z) | ¹H-NMR |
|---|---|---|---|
| A-8 | 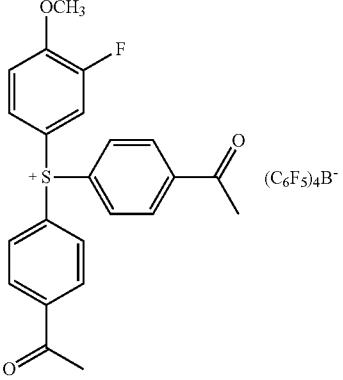 | 395 | 2.5043 (6H, s), 3.8421 (3H, s), 6.8120-7.9602 (11H, m) |
| A-9 | 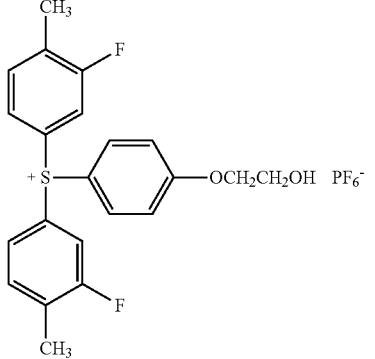 | 387 | 2.0100 (1H, s), 2.3312 (6H, s), 3.9510-4.1325 (5H, m), 6.8120-7.2302 (10H, m) |
| A-10 | 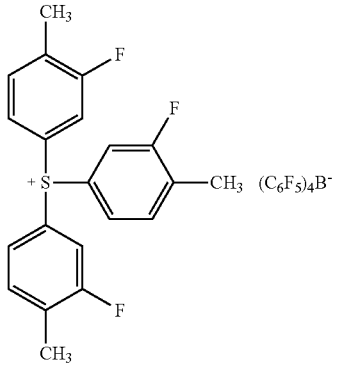 | 354 | 2.3312 (12H, s), 6.9920-7.1402 (9H, m) |
| A-11 | 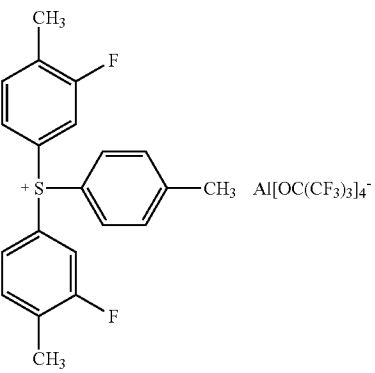 | 341 | 2.3312 (9H, s), 2.3742 (3H, s), 6.9938-7.1618 (10H, m) |

TABLE 1-continued

| Compound | Structure | MS (m/Z) | ¹H-NMR |
|---|---|---|---|
| A-12 | 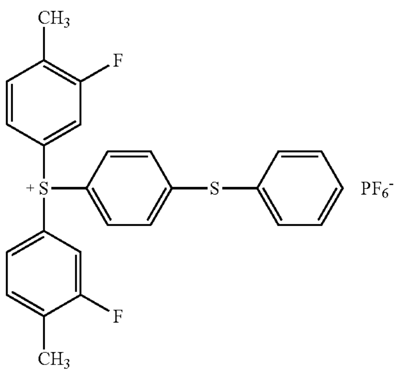 | 435 | 2.3312 (6H, s), 6.8038-7.2218(15H, m) |
| A-13 | 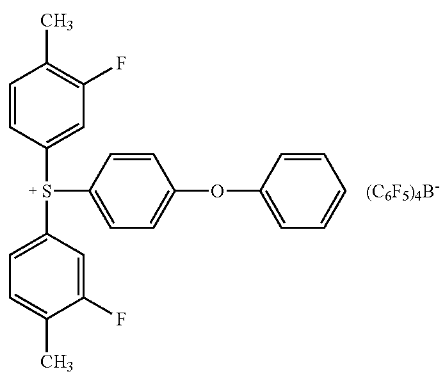 | 419 | 2.3312 (6H, s), 6.9214-7.2218(15H, m) |
| A-14 | 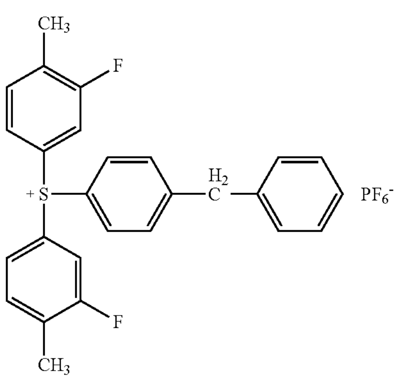 | 417 | 2.3312 (6H, s), 3.8123 (2H, s), 6.9214-7.1438(15H, m) |
| A-15 | 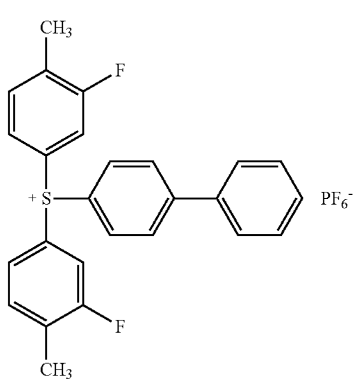 | 403 | 2.3312 (6H, s), 6.9923-7.7738(15H, m) |

TABLE 1-continued
| Compound | Structure | MS (m/Z) | ¹H-NMR |
|---|---|---|---|
| A-16 | 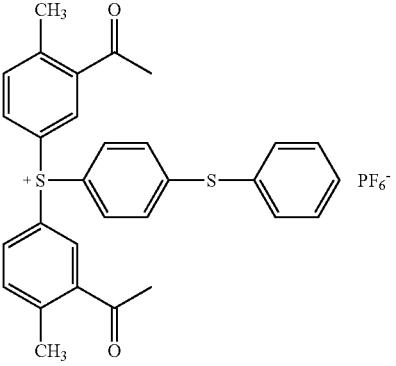 | 455 | 2.4811 (6H, s), 2.5034 (6H, s), 7.2732-7.8838(15H, m) |
| A-17 | 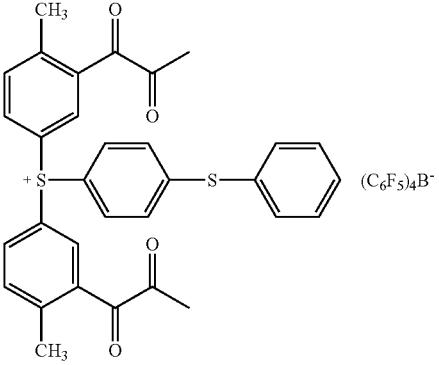 | 511 | 2.1722 (6H, s), 2.4861 (6H, s), 7.1321-7.8323(15H, m) |
| A-18 | 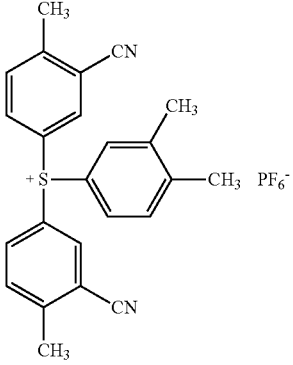 | 369 | 2.2312-2.2912 (6H, m), 2.4033 (6H, s), 7.1121-7.5613(9H, m) |
| A-19 | 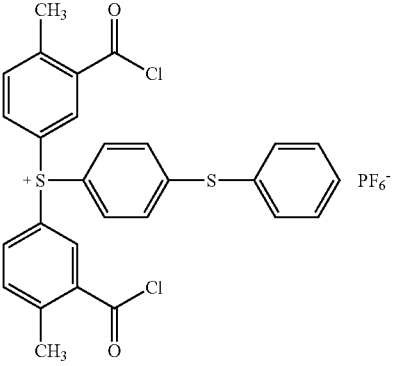 | 524 | 2.4854 (6H, s), 7.3722-8.0912(15H, m) |

TABLE 1-continued
| Compound | Structure | MS (m/Z) | ¹H-NMR |
|---|---|---|---|
| A-20 | 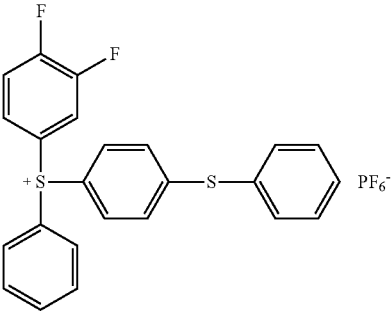 | 407 | 7.0213-7.4424(17H, m) |
| A-21 | 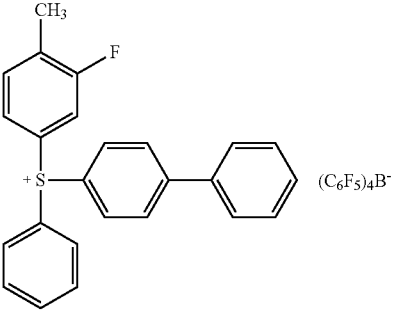 | 371 | 2.3312 (3H, s), 6.9012-7.4856(17H, m) |
| A-22 | 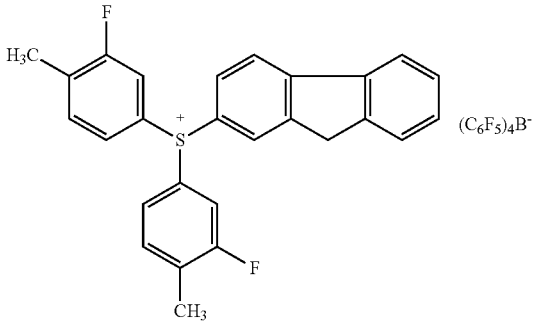 | 415 | 2.3312 (6H, s), 3.9127 (2H, s), 6.8024-7.8254(13H, m) |
| A-23 | 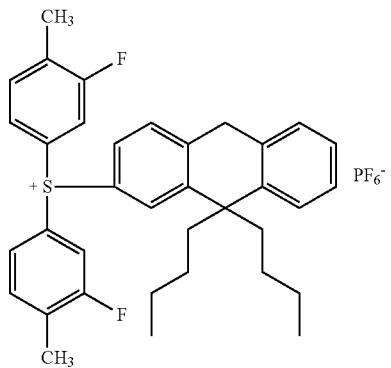 | 527 | 0.9612(6H, m), 1.2943-1.8723(6H, m), 2.3312 (6H, s), 6.8024-7.8254(13H, m) |

TABLE 1-continued
| Compound | Structure | MS (m/Z) | ¹H-NMR |
|---|---|---|---|
| A-24 | 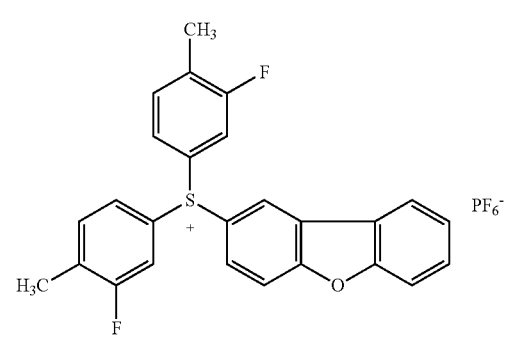 | 417 | 2.3312 (6H, s), 6.9932-7.9832(13H, m) |
| A-25 | 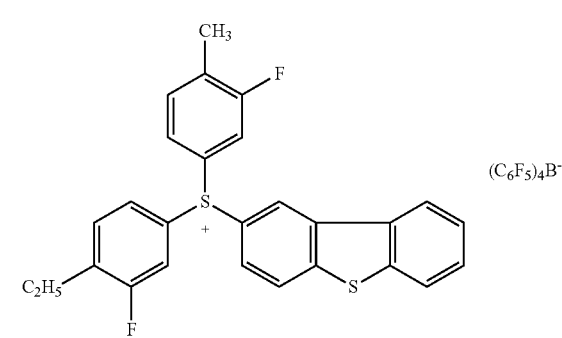 | 461 | 1.1823-2.7146 (10H, m), 7.0433-7.9612(13H, m) |
| A-26 | 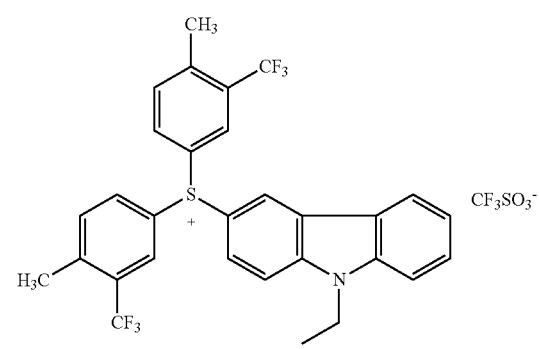 | 572 | 1.3765-1.3771 (3H, m), 2.2943 (6H, s), 4.5342 (2H, m), 7.0933-8.1743(13H, m) |
| A-27 | 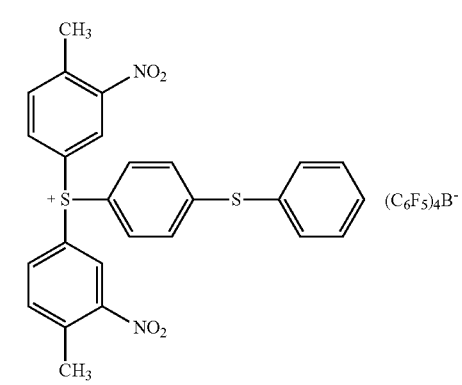 | 489 | 2.5412 (6H, s), 7.0612-8.2131(15H, m) |

TABLE 1-continued

| Compound | Structure | MS (m/Z) | ¹H-NMR |
|---|---|---|---|
| A-28 | [Structure: sulfonium cation with two 3-fluoro-4-ethylphenyl groups and one 4-methoxyphenyl group, (CF₃CF₂)₂PF₄⁻ counterion] | 385 | 1.2423(6H, m), 2.5933 (4H, m), 3.7324 (3H, s), 6.8024-7.2354(10H, m) |
| A-29 | [Structure: sulfonium cation with two 3-fluoro-4-methylphenyl groups and one 4-((4-acetylphenyl)thio)phenyl group, $PF_6^-$ counterion] | 501 | 2.3312 (6H, s), 2.5034(3H, s), 7.0532-7.7048(14H, m) |
| A-30 | [Structure: sulfonium cation with two 3-fluoro-4-methylphenyl groups and one 4-((4-benzoylphenyl)thio)phenyl group, $PF_6^-$ counterion] | 565 | 2.3312 6H s), 6.9931-7.8148(19H, m) |
| A-31 | [Structure: sulfonium cation with two 3-trifluoromethyl-4-ethylphenyl groups and one 4-methoxyphenyl group, (C₆F₅)₄B⁻ counterion] | 485 | 1.2423(6H, m), 2.5933 (4H, m), 3.7324 (3H, s), 6.8024-7.2354(10H, m) |

TABLE 1-continued

| Compound | Structure | MS (m/Z) | ¹H-NMR |
|---|---|---|---|
| A-32 | (structure) | 469 | 1.2423(6H, m), 2.0100 (1H, s), 2.5933 (4H, m), 3.9524-4.1335 (4H, m), 6.8024-7.2354(10H, m) |
| A-33 | (structure) | 495 | 1.2423(6H, m), 2.5512 (6H, s), 3.9524-4.1335 (4H, m), 6.9224-7.8654(15H, m) |
| A-34 | (structure) | 427 | 1.2934(6H, d), 2.5512 (3H, s), 7.0021-7.8654(17H, m) |
| A-35 | (structure) | 467 | 3.7321 (6H, s), 6.8024-7.2354(15H, m) |

TABLE 1-continued
| Compound | Structure | MS (m/Z) | ¹H-NMR |
|---|---|---|---|
| A-36 | 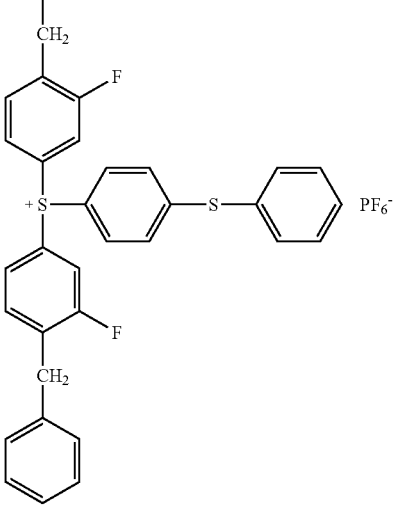 | 587 | 3.8178 (4H, s), 6.9018-7.2054(25H, m) |
| A-37 | 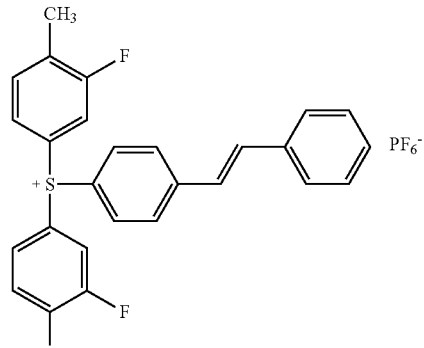 | 429 | 2.3312 (6H, s), 6.9912(2H, d), 6.8024-7.4454(15H, m) |
| A-38 | 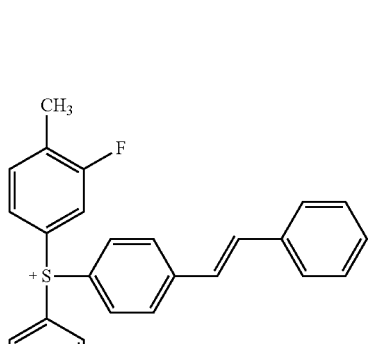 | 397 | 2.3312 (3H, s), 6.8024-7.4454(17H, m) |

Regarding the Triphenylsulfonium Salt Compound Having the General Formula (II)

PREPARATION EXAMPLES

Example II-1: Preparation of Sulfonium Salt C-1

(1) Intermediate a1

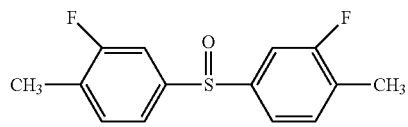

To 500 mL four-necked flask 110.0 g of o-fluorotoluene, 59.5 g of dichlorosulfoxide, and 200 mL of dichloromethane were charged, and cooled in an ice-water bath. The temperature was controlled at approximately 5° C. 66.5 g of aluminium trichloride was added in batches over about 1 hour. It was stirred for additional 2 hours, and the liquid phase was tracked until the reaction was completed. The solution of the product in dichloromethane was poured into 500 g of ice water, and continuously stirred. The dichloromethane layer was separated and washed with water, followed by rotary evaporation of the dichloromethane product solution, to obtain 106 g of light yellow solid, i.e., Intermediate a1 (yield: 79.7%, HPLC purity: 98%).

The product structure of the intermediate was confirmed by H-NMR and MS, and the specific characterization results are as follows:

$^1$H-NMR (CDCl$_3$, 500 MHz): 2.3512 (6H, s), 7.2438-7.3305 (6H, m).

MS (m/Z): 267 (M+H)$^+$.

(2) Intermediate b'1

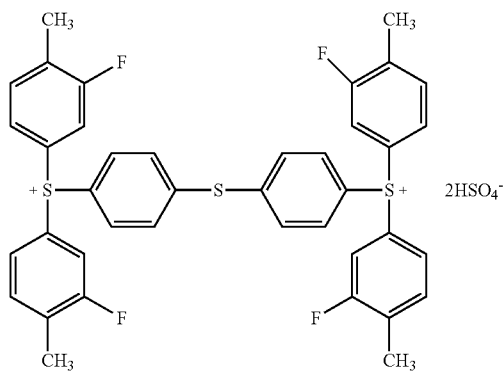

To 500 mL four-necked flask 66.5 g of Intermediate a1 and 200 mL of acetic anhydride were charged, and stirred in an ice-water bath. The temperature was controlled at approximately 0° C. 35 g of concentrated sulfuric acid (mass fraction: 70%) was dropwise added over about 1 hour. After the completion of dropwise addition, to the reaction system 23.3 g of phenyl sulfide was added in batches, and stirred for additional 12 hours. Then 100 mL of deionized ice water was slowly dropwise added. The solution was extracted by benzene 2-3 times, the aqueous layer was separated, and the combined benzene layer was washed with water once. The aqueous layers were combined, to obtain the aqueous solution of Intermediate b'1.

(3) Target Product i.e., Compound C-1

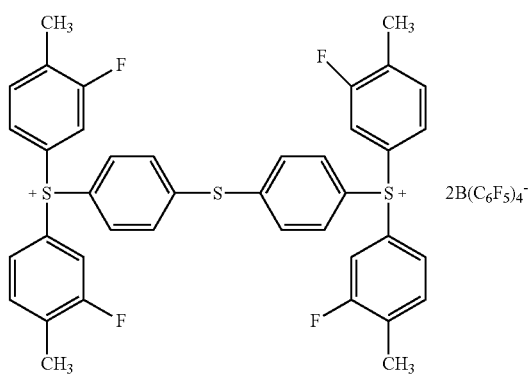

To the above aqueous solution of Intermediate b'1 179.5 g of potassium tetra-(pentafluorophenyl)borate solid was added for ion exchange, and deionized water was appropriately supplemented under stirring. As the dissolution of potassium tetra-(pentafluorophenyl)borate solid, target product C-1 gradually precipitated, and was filtered and dried, to obtain 158 g of white solid (yield: 62.0%, HPLC purity: 99%).

The structure of the target product was confirmed by H-NMR and MS, and the specific characterization results are as follows:

$^1$H-NMR (CDCl$_3$, 500 MHz): 2.3512 (12H, s), 6.8038-7.2818 (20H, m).

MS (m/Z): 684 (M)*.

Example II-2

Referring to the preparation method of Example 11-1, using dichlorosulfoxide and corresponding substituted benzene as starting materials, Compounds C2-C25 as shown in Table 2 were prepared.

The structures of target products as well as their MS (m/Z) and $^1$H-NMR data were listed in Table 2.

TABLE 2
| Compound | Structure | MS (m/Z) | $^1$H-NMR |
|---|---|---|---|
| C-2 | 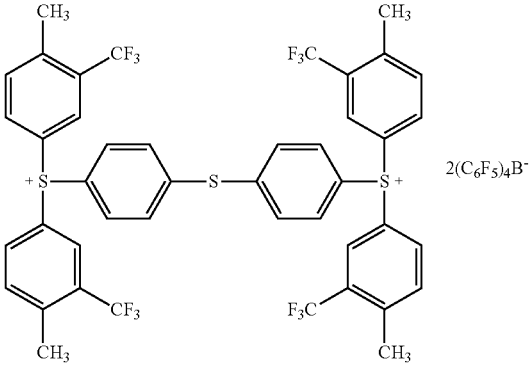 | 884 | 2.1234 (12H, s), 6.8138-7.4918(20H, m) |
| C-3 | 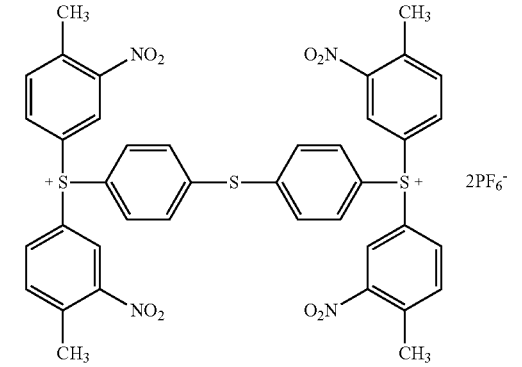 | 792 | 2.5423 (12H, s), 7.1382-8.2132(20H, m) |
| C-4 | 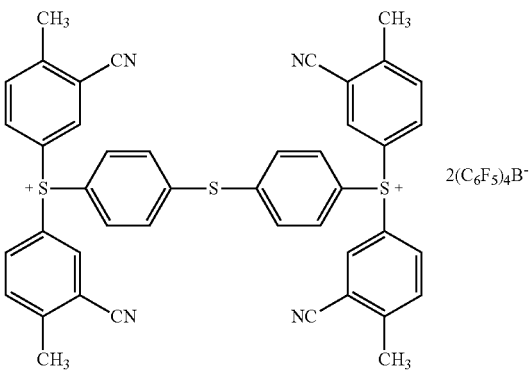 | 712 | 2.4056 (12H, s), 6.9512-7.5632(20H, m) |
| C-5 | 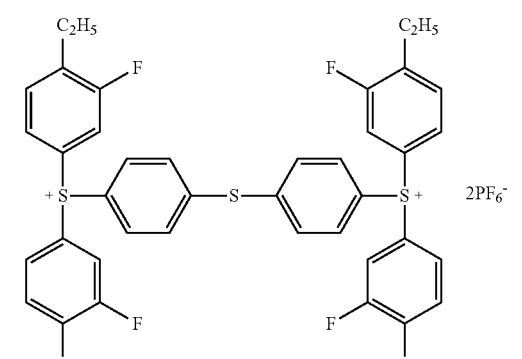 | 740 | 1.1856-2.7123 (20H, m), 7.0478-7.3824(20H, m) |

TABLE 2-continued
| Compound | Structure | MS (m/Z) | ¹H-NMR |
|---|---|---|---|
| C-6 | 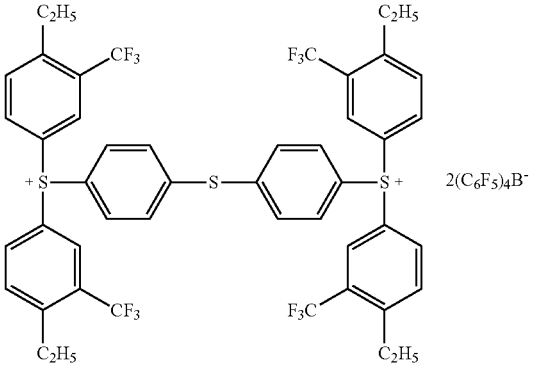 2(C₆F₅)₄B⁻ | 941 | 1.1856-2.7123 (20H, m), 7.1323-7.5234(20H, m) |
| C-7 | 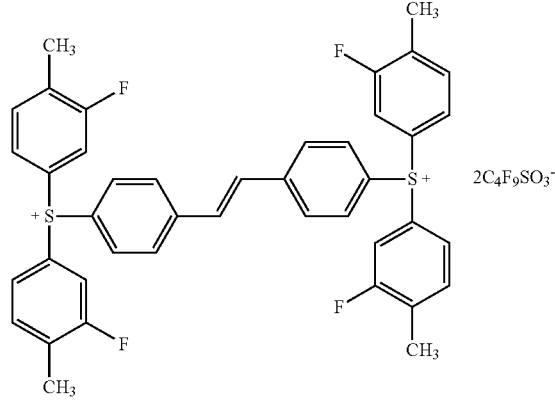 2C₄F₉SO₃⁻ | 678 | 2.3312 (12H, s), 6.9012 (2H, d), 7.0513-7.4634(20H, m) |
| C-8 | 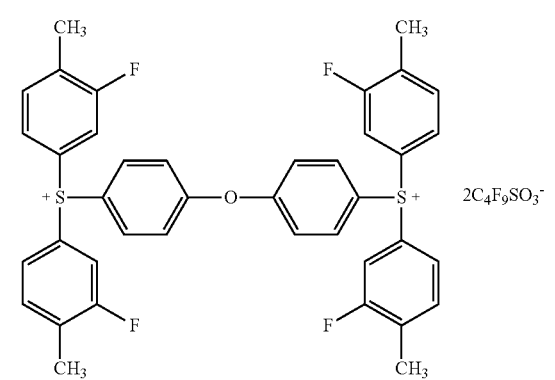 2C₄F₉SO₃⁻ | 668 | 2.3312 (12H, s), 6.9945-7.2934(20H, m) |
| C-9 | 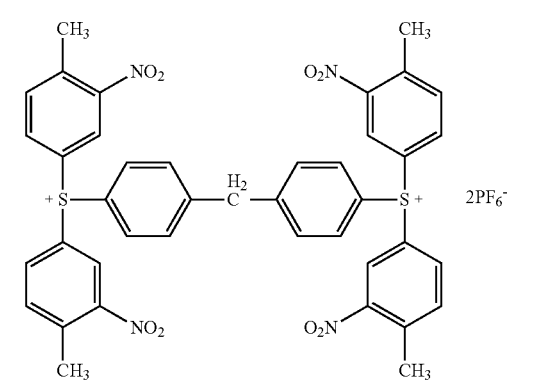 2PF₆⁻ | 774 | 2.5467 (12H, s), 4.0912 (2H, s), 7.1823-8.2134(20H, m) |

TABLE 2-continued
| Compound | Structure | MS (m/Z) | ¹H-NMR |
|---|---|---|---|
| C-10 | 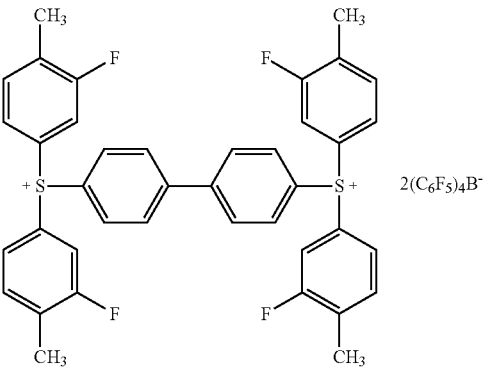 2(C₆F₅)₄B⁻ | 652 | 2.3312 (12H, s), 6.9945-7.7720(20H, m) |
| C-11 | 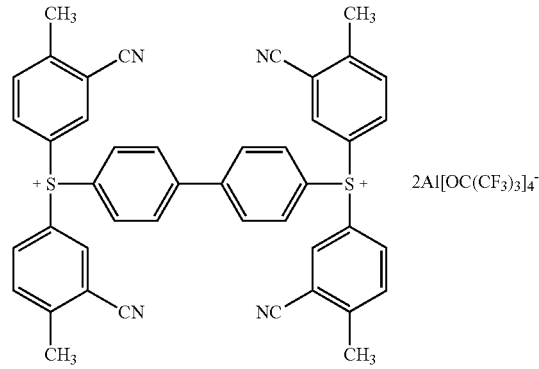 2Al[OC(CF₃)₃]₄⁻ | 680 | 2.4012 (12H, s), 7.3455-7.7720(20H, m) |
| C-12 | 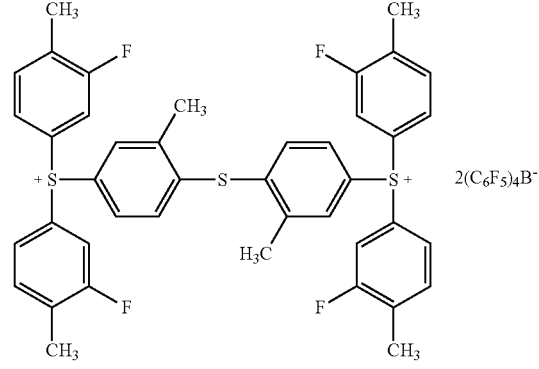 2(C₆F₅)₄B⁻ | 712 | 2.3312 (12H, s), 2.3401 (6H, s), 6.9945-7.3312(18H, m) |
| C-13 | 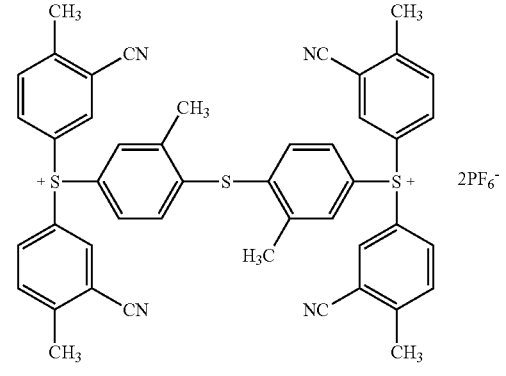 2PF₆⁻ | 741 | 2.3401 (6H, s), 2.4056 (12H, s), 7.0123-7.5632(18H, m) |

TABLE 2-continued
| Compound | Structure | MS (m/Z) | ¹H-NMR |
|---|---|---|---|
| C-14 | 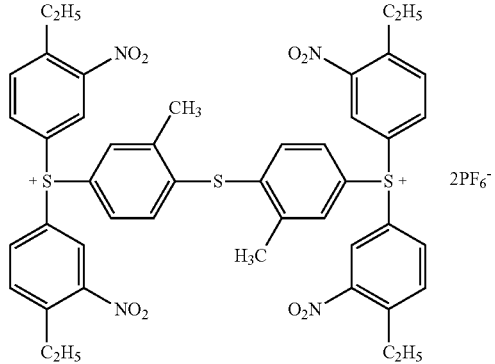 | 797 | 1.1856-2.7123 (26H, m), 7.0123-8.2634(18H, m) |
| C-15 | 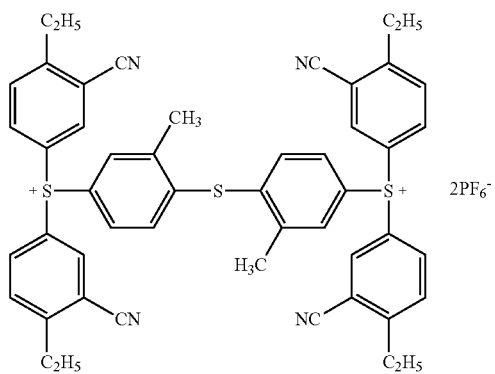 | 888 | 1.1856-2.7123 (26H, m), 7.0123-7.6123 (18H, m) |
| C-16 | 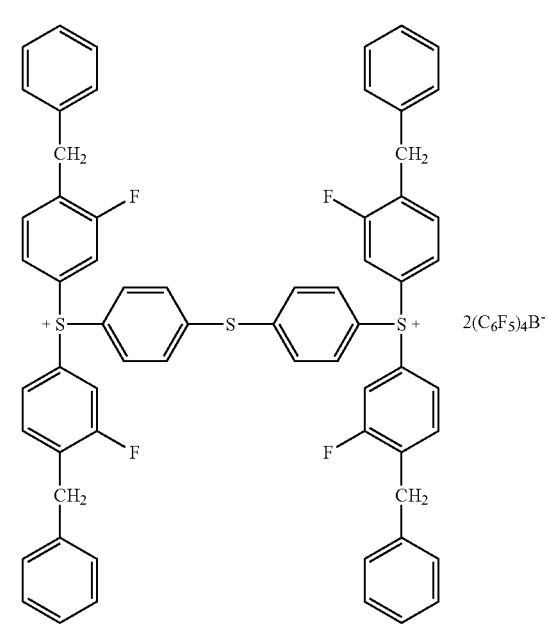 | 989 | 3.9934 (8H, s), 7.0945-7.3889 (40H, m) |

TABLE 2-continued
| Compound | Structure | MS (m/Z) | ¹H-NMR |
|---|---|---|---|
| C-17 | 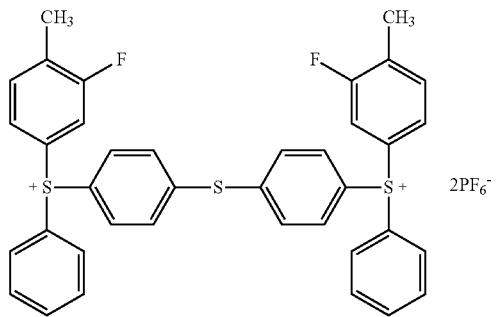 2PF$_6^-$ | 620 | 2.3343 (6H, s), 6.9943-7.3832 (24H, m) |
| C-18 | 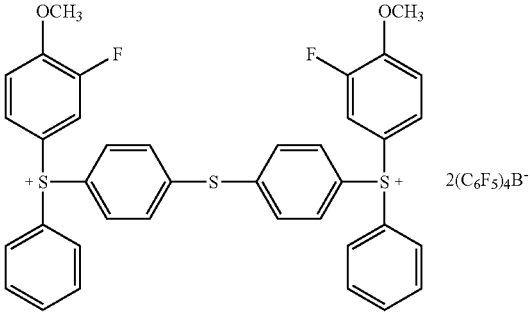 2(C$_6$F$_5$)$_4$B$^-$ | 652 | 3.8323 (6H, s), 5.2134-5.2232 (2H, d) 6.9432-7.4922 (22H, m) |
| C-19 | 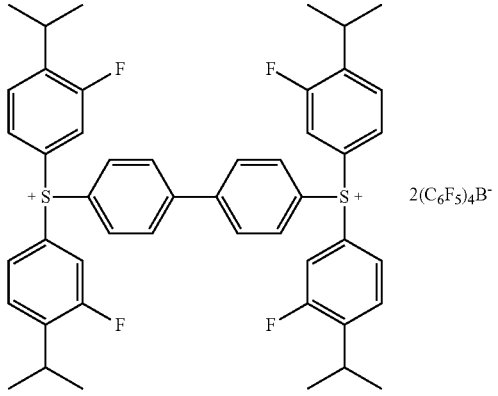 2(C$_6$F$_5$)$_4$B$^-$ | 765 | 1.1832-2.8843 (28H, m), 7.0432-7.7732 (20H, m) |
| C-20 | 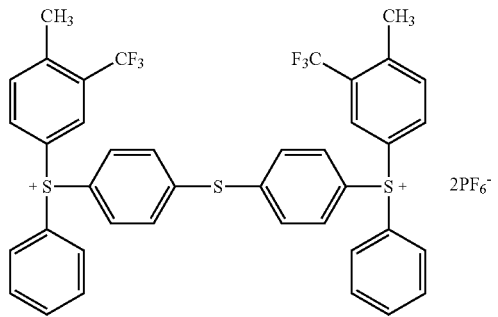 2PF$_6^-$ | 720 | 2.2943 (6H, s), 6.2067-7.7932 (22H, m) |

TABLE 2-continued
| Compound | Structure | MS (m/Z) | ¹H-NMR |
|---|---|---|---|
| C-21 | 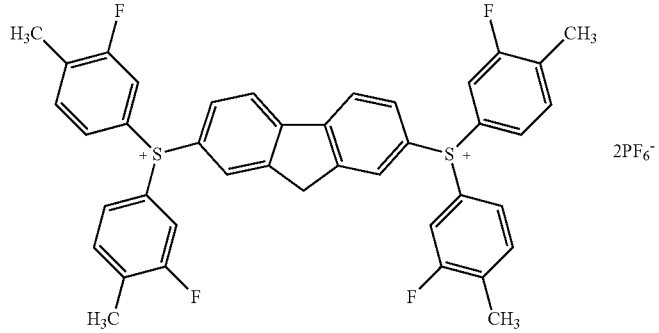 2PF₆⁻ | 664 | 2.3312 (12H, s), 4.1222 (2H, s), 6.9943-7.9013 (18H, m) |
| C-22 | 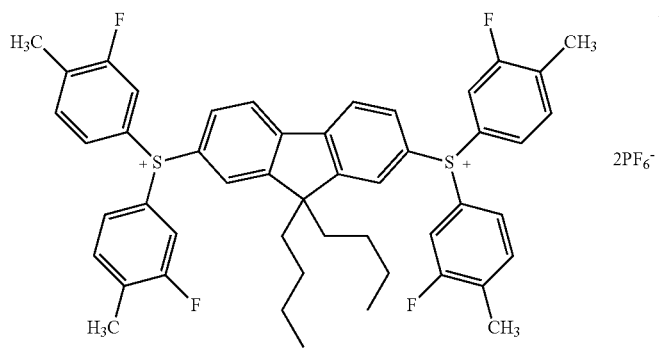 2PF₆⁻ | 776 | 0.8856-1.8845 2.3312 (12H, s), 6.9943-7.9013 (18H, m) |
| C-23 | 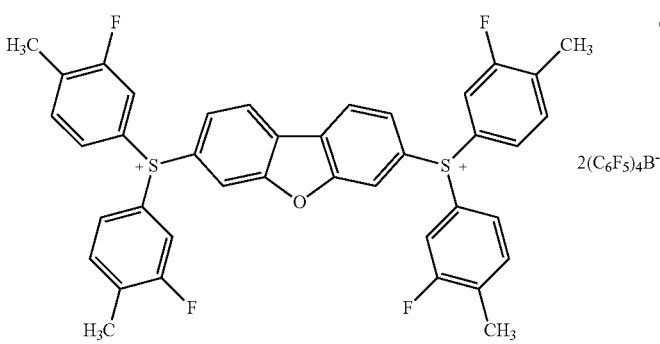 2(C₆F₅)₄B⁻ | 668 | 2.3312 (12H, s), 6.9943-7.8478 (18H, m) |
| C-24 | 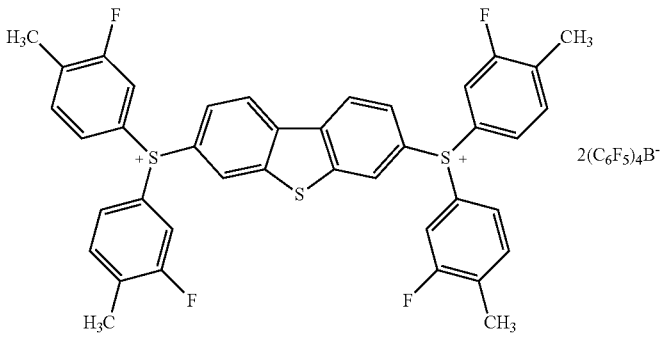 2(C₆F₅)₄B⁻ | | 2.3312 (12H, s), 6.9943-8.0563 (18H, m) |

TABLE 2-continued

| Compound | Structure | MS (m/Z) | ¹H-NMR |
|---|---|---|---|
| C-25 | 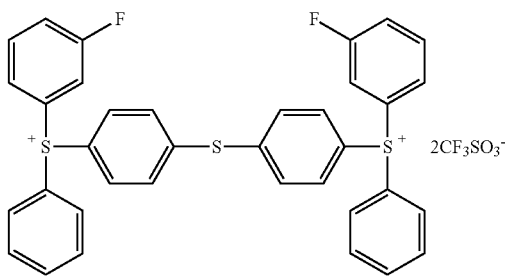 | 892 | 1.3745-1.3767 (3H, m) 2.2948 (12H, s), 4.5366 (2H, m), 7.0923-8.2435 (18H, m) |

Performance Evaluation

By formulating exemplary photo-curable compositions, the application performance as photoinitiator was tested for the compounds represented by general formulae (I) and (II) in the present invention.

1. Dissolution Performance Test

The solubility in 3-ethyl-3-hydroxymethyl oxetane monomer was tested for Compound A-1 to A-38 and C-1 to C-25, and comparative compounds B-1 and B-2 as well as D-1 and D-2 in the present invention, calculated based on the maximum number of grams dissolved in 100 g solvent at 20° C.

Compound B-1

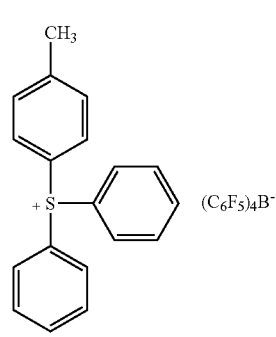

Compound B-2

Compound D-1

Compound D-2

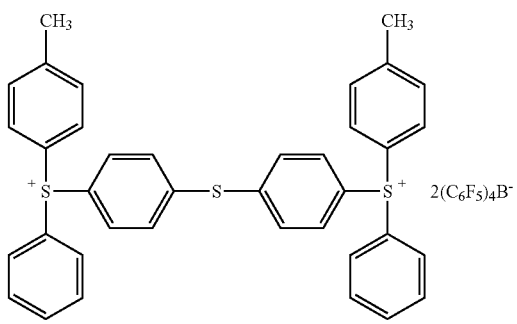

The test results are shown in Table 3 and Table 4.

2. Acid Production Rate Test

The above compounds were formulated into 0.02 mmol/g acetonitrile solutions, respectively. To a dish with an inner diameter of 100 mm, 5.00 g of formulated acetonitrile solution was added, and then 200 mj/cm² of energy was cumulatively accepted with a light intensity of 0.8 mw/cm² under the irradiation of an ultraviolet lamp (model FL10BL). The solution after exposure was titrated with 0.05N solution of potassium hydroxide in ethanol, using BTB as an indicator. The corresponding solution prior to the irradiation was titrated to obtain blank value. By subtracting the blank value from the titration measurement value, the acid production rate was calculated based on the following equation:

Acid production rate %=(acid titration value−blank value) (mol)/theoretical mole number of the compound (mol)×100%.

The test results are shown in Table 3 and Table 4.

3. Photosensitivity Test

By formulating an exemplary photoresist, the photosensitivity was tested for the compounds represented by general formula (I) and (II) in the present invention.

The composition of photoresist was as follows:

| | |
|---|---|
| resin A | 40 parts by mass, |
| resin B | 60 parts by mass, |
| photoinitiator | 1 part by mass, |
| solvent (PGMEA) | 150 parts by mass. | wherein
resin A represents

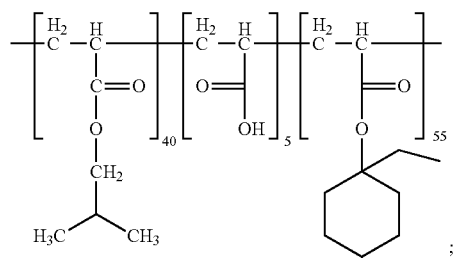

;

The resin B represents a nevolac resin obtained by condensation of m-cresol and p-cresol at a molar ratio of 1:1 under the catalytic condition of formaldehyde and acid, with a molecular weight of approximately 10,000;

The above-mentioned compounds A-1 to A-38, C-1 to C-25 or comparative compound B-1 and B-2 as well as D-1 and D-2 were used as photoinitiators.

The components were stirred uniformly in the above proportions, and filtered through a membrane filter with a pore size of 1 μm, to prepare a resist composition with a solid content of 40%.

The resist composition was uniformly coated on the silicon wafer substrate by a spin coater, and oven dried to obtain a 20 μm thick photoresist coating. It was pre-baked at 130° C. for 6 minutes. Then TME-150RSC was used for pattern exposure (line i), wherein the exposure was conducted using a hot plate at 75° C. for 5 minutes. Then, it was developed with a tetramethylammonium hydroxide solution (mass fraction 2.38%) for 5 minutes, then washed with running water, and blow dried by nitrogen, to obtain a 10 μm line pattern. The minimum exposure amount under which no pattern residues can be seen (i.e., the minimum exposure amount required to form the resist pattern) was determined. The lower the value, the higher the photosensitivity of the initiator was.

The test results are shown in Table 3 and Table 4.

TABLE 3

| Example/Comparative Example | Compound | Solubility (g) | Acid production rate (%) | Minimum exposure amount (mj/cm$^2$) |
|---|---|---|---|---|
| Example 1 | A-1 | 25.7 | 85 | 120 |
| Example 2 | A-2 | 23.5 | 81 | 140 |
| Example 3 | A-3 | 22.5 | 80 | 150 |
| Example 4 | A-4 | 19.5 | 72 | 180 |
| Example 5 | A-5 | 19.1 | 68 | 200 |
| Example 6 | A-6 | 19.2 | 78 | 160 |
| Example 7 | A-7 | 20.6 | 65 | 200 |
| Example 8 | A-8 | 23.4 | 75 | 170 |
| Example 9 | A-9 | 24.3 | 86 | 100 |
| Example 10 | A-10 | 23.8 | 80 | 160 |
| Example 11 | A-11 | 21.6 | 75 | 170 |
| Example 12 | A-12 | 24.5 | 88 | 110 |
| Example 13 | A-13 | 23.8 | 72 | 180 |
| Example 14 | A-14 | 23.5 | 85 | 110 |
| Example 15 | A-15 | 23.4 | 84 | 120 |
| Example 16 | A-16 | 22.6 | 82 | 120 |
| Example 17 | A-17 | 21.5 | 76 | 170 |
| Example 18 | A-18 | 23.2 | 85 | 110 |
| Example 19 | A-19 | 24.3 | 82 | 120 |
| Example 20 | A-20 | 19.8 | 75 | 170 |
| Example 21 | A-21 | 20.1 | 70 | 200 |
| Example 22 | A-22 | 22.3 | 78 | 160 |
| Example 23 | A-23 | 23.5 | 85 | 110 |
| Example 24 | A-24 | 23.1 | 83 | 120 |
| Example 25 | A-25 | 22.8 | 80 | 150 |
| Example 26 | A-26 | 22.6 | 70 | 200 |
| Example 27 | A-27 | 22.3 | 78 | 170 |
| Example 28 | A-28 | 26.4 | 85 | 120 |
| Example 29 | A-29 | 25.8 | 82 | 120 |
| Example 30 | A-30 | 27.8 | 83 | 110 |
| Example 31 | A-31 | 27.6 | 76 | 180 |
| Example 32 | A-32 | 28.2 | 80 | 150 |
| Example 33 | A-33 | 24.3 | 74 | 180 |
| Example 34 | A-34 | 26.2 | 70 | 200 |
| Example 35 | A-35 | 24.8 | 81 | 140 |
| Example 36 | A-36 | 23.2 | 83 | 110 |
| Example 37 | A-37 | 22.4 | 85 | 110 |
| Example 38 | A-38 | 23.5 | 74 | 180 |
| Comparative Example 1 | B-1 | 12.1 | 70 | 200 |
| Comparative Example 2 | B-2 | 20.6 | 43 | More than 300 |

It can be seen from the test results in Table 3 that, the sulfonium salt compound of the present invention exhibits satisfactory solubility, and has excellent acid production rate and photosensitive activity. Compared with the existing improved triphenylsulfonium salts B-1 and B-2, it has significantly advantageous performance as well as broad use prospects.

TABLE 4

| Example/Comparative Example | Compound | Solubility (g) | Acid production rate (%) | Minimum exposure amount (mj/cm$^2$) |
|---|---|---|---|---|
| Example 1 | C-1 | 24.4 | 87 | 100 |
| Example 2 | C-2 | 24.3 | 84 | 110 |
| Example 3 | C-3 | 23.4 | 89 | 90 |
| Example 4 | C-4 | 23.1 | 82 | 120 |
| Example 5 | C-5 | 25.1 | 92 | 80 |
| Example 6 | C-6 | 25.3 | 84 | 110 |
| Example 7 | C-7 | 22.4 | 82 | 120 |
| Example 8 | C-8 | 23.7 | 80 | 130 |
| Example 9 | C-9 | 23.1 | 82 | 120 |
| Example 10 | C-10 | 21.4 | 79 | 140 |
| Example 11 | C-11 | 21.0 | 78 | 140 |
| Example 12 | C-12 | 25.3 | 84 | 110 |
| Example 13 | C-13 | 24.9 | 80 | 130 |
| Example 14 | C-14 | 25.6 | 81 | 120 |
| Example 15 | C-15 | 25.4 | 81 | 120 |
| Example 16 | C-16 | 24.4 | 77 | 150 |
| Example 17 | C-17 | 21.5 | 74 | 180 |
| Example 18 | C-18 | 20.7 | 72 | 190 |
| Example 19 | C-19 | 24.8 | 78 | 140 |
| Example 20 | C-20 | 22.1 | 75 | 170 |
| Example 21 | C-21 | 23.4 | 80 | 130 |
| Example 22 | C-22 | 24.5 | 78 | 140 |
| Example 23 | C-23 | 23.6 | 77 | 150 |
| Example 24 | C-24 | 23.5 | 77 | 150 |

TABLE 4-continued

| Example/Comparative Example | Compound | Solubility (g) | Acid production rate (%) | Minimum exposure amount (mj/cm²) |
|---|---|---|---|---|
| Example 25 | C-25 | 22.8 | 75 | 170 |
| Comparative Example 1 | D-1 | 11.5 | 74 | 180 |
| Comparative Example 2 | D-2 | 19.3 | 49 | More than 300 |

It can be seen from the test results in Table 4 that, the bis-triphenylsulfonium salt compound represented by general formula (II) in the present invention exhibits satisfactory solubility, and has excellent acid production rate and photosensitive activity. Compared with the existing improved triphenylsulfonium salts D-1 and D-2, it has significantly advantageous performance as well as broad application prospects.

The above descriptions are merely preferred embodiments of the present invention and are not intended to limit the present invention. For those skilled in the art, the present invention may have various modifications and changes. Any modification, equivalent replacement, and improvement made within the spirit and principle of the present invention shall be included within the scope of the present invention.

What is claimed is:

1. A triphenylsulfonium salt compound, having a structure represented by the following general formula (II) or general formula (III) or general formula (IV):

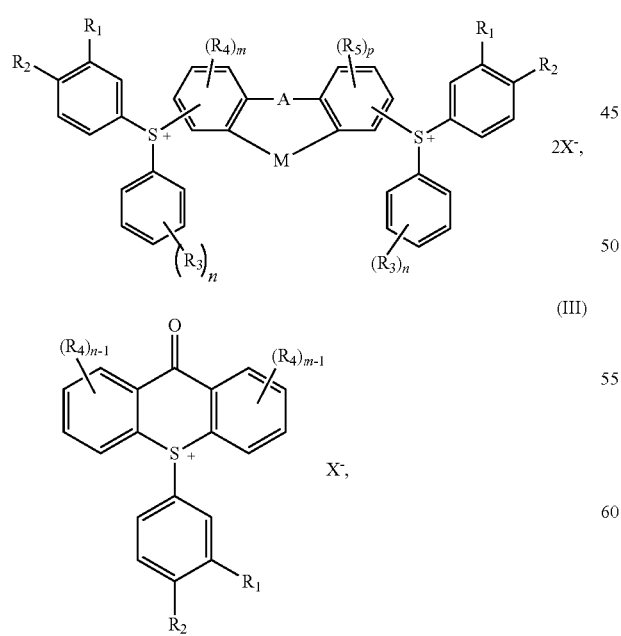

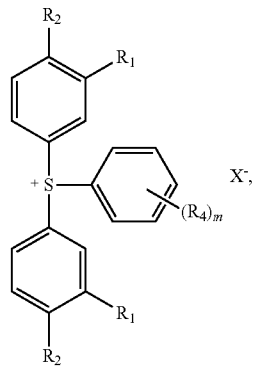

wherein, $R_1$ represents an electron-withdrawing group, selected from the group consisting of halogen, cyano, nitro, alkoxy, haloalkyl, acyl, acyloxy, and sulfonyl;

$R_2$ represents an amplification group, selected from the group consisting of halogen, substituted or unsubstituted alkyl, substituted or unsubstituted alkoxy, and substituted or unsubstituted aralkyl;

each $R_3$ independently represents any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; the carbon-carbon bond in the groups representing $R_3$ in the general formula (II) may be interrupted by —O— or —S—, and $R_3$ groups may be connected with each other to form a ring;

each $R_4$ and $R_5$ independently represent any of halogen, nitro, cyano, hydroxy, acyl, acyloxy, sulfonyl, substituted or unsubstituted alkyl, substituted or unsubstituted alkoxy, substituted or unsubstituted aryl, and substituted or unsubstituted aralkyl; optionally, —$CH_2$— in the groups representing $R_4$ in the general formula (IV) may be replaced with —O—, —S—, or —CH=CH—, the carbon-carbon bond in the groups representing $R_4$ and $R_5$ in the general formula (II) may be interrupted by —O— or —S—, and $R_4$ groups may be connected with each other to form a ring, and $R_5$ groups may be connected with each other to form a ring;

in the general formula (IV), m represents 0, 1, or 2; wherein when m is 1, $R_4$ in the general formula (IV) is located at the para-position of S in the benzene ring group, and when m is 2, adjacent $R_4$s together with phenyl connected with $R_4$ form a ring;

in the general formula (II), n represents any integer of 0 to 5, and m and p each independently represent any integer of 0 to 4; and in the general formula (III), n and m each independently represent an integer of 1 to 5, $X^-$ represents a non-nucleophilic anion, and in the general formula (II), A and M each independently represent a linking group.

2. The triphenylsulfonium salt compound according to claim 1, characterized in that: $R_1$ is selected from any of halogen, cyano, nitro, haloalkyl, and acyl.

3. The triphenylsulfonium salt compound according to claim 2, characterized in that: the halogen as $R_1$ is fluorine, chlorine, bromine, or iodine.

4. The triphenylsulfonium salt compound according to claim 2, characterized in that: the alkoxy as $R_1$ is any of $C_1$-$C_8$ linear or branched alkoxy.

5. The triphenylsulfonium salt compound according to claim 2, characterized in that: the alkyl in haloalkyl as $R_1$ is $C_1$-$C_8$ linear alkyl, or $C_3$-$C_8$ branched alkyl, or $C_3$-$C_8$ cycloalkyl.

6. The triphenylsulfonium salt compound according to claim 2, characterized in that: the acyl as $R_1$ or the acyl in acyloxy as $R_1$ each independently has a structure represented by

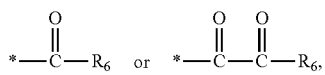

wherein $R_6$ represents any of hydrogen, halogen, substituted or unsubstituted alkyl, substituted or unsubstituted aryl, and substituted or unsubstituted aralkyl.

7. The triphenylsulfonium salt compound according to claim 2, characterized in that: the sulfonyl as $R_1$ is methanesulfonyl, difluoromethanesulfonyl, trifluoromethanesulfonyl, benzenesulfonyl, or toluenesulfonyl.

8. The triphenylsulfonium salt compound according to claim 1, characterized in that: $R_2$ in the general formula (II) is selected from any of substituted or unsubstituted alkyl, substituted or unsubstituted alkoxy, and substituted or unsubstituted aralkyl.

9. The triphenylsulfonium salt compound according to claim 8, characterized in that: the alkyl as $R_2$ is unsubstituted $C_1$-$C_8$ linear alkyl or $C_3$-$C_8$ branched alkyl.

10. The triphenylsulfonium salt compound according to claim 8, characterized in that: the alkoxy as $R_2$ is unsubstituted, wherein the alkyl in alkoxy is unsubstituted $C_1$-$C_8$ linear alkyl or $C_3$-$C_8$ branched alkyl.

11. The triphenylsulfonium salt compound according to claim 8, characterized in that: the aralkyl as $R_2$ is phenyl-terminated $C_1$-$C_8$ alkyl.

12. The triphenylsulfonium salt compound according to claim 1, characterized in that: in the general formula (IV) and the general formula (II), n is 0.

13. The triphenylsulfonium salt compound according to claim 1, characterized in that: in the general formula (II), n is 2, and two $R_3$ represent $R_1$ and $R_2$ respectively, and the compound has a structure represented by general formula (V):

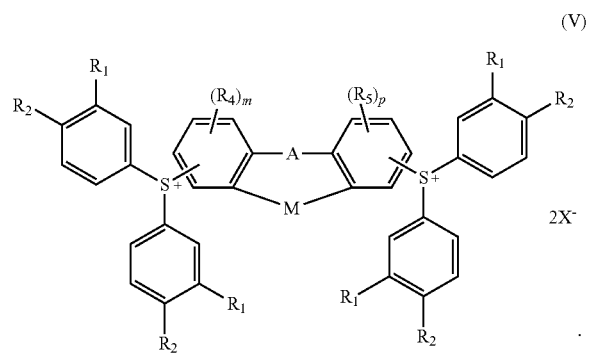

14. The triphenylsulfonium salt compound according to claim 1, characterized in that: in the general formula (II), m represents 0, 1, or 2; when m is 1, $R_4$ in the general formula (II) is located at the ortho-position of group A in the benzene ring group.

15. The triphenylsulfonium salt compound according to claim 1, characterized in that: $X^-$ represents $M^-$, $ClO_4^-$, $CN^-$, $HSO_4^-$, $NO_3^-$, $CF_3COO^-$, $(BM_4)^-$, $(SbM_6)^-$, $(AsM_6)^-$, $(PM_6)^-$, $Al[OC(CF_3)_3]_4^-$, $R_7SO_3^-$, $(R_7SO_2)_3C^-$, $(R_7SO_2)_2N^-$, $B(C_6M_5)_4^-$, $Ga(C_6M_5)_4^-$, or $[(Rf)_bPF_{6-b}]^-$, wherein M represents halogen, $R_7$ represents any of $C_1$-$C_{20}$ alkyl, $C_1$-$C_{20}$ perfluoroalkyl, $C_6$-$C_{20}$ aryl, or substituted aryl, Rf represents alkyl in which ≥80% of hydrogen atoms are replaced with fluorine atoms, b represents any integer of 1 to 5, and each Rf group may be identical to or different from each other.

16. The triphenylsulfonium salt compound according to claim 1, characterized in that: p represents 0, 1, or 2, and when p represents 1, $R_5$ is located at the ortho-position of group A in the benzene ring group.

17. The triphenylsulfonium salt compound according to claim 1, characterized in that: A represents a linking bond, *O*, *S*, alkylene, or alkenylene.

18. The triphenylsulfonium salt compound according to claim 1, characterized in that: M represents blank,

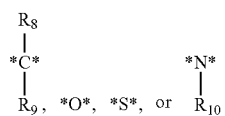

group, wherein $R_8$, $R_9$, and $R_{10}$ each independently represent any of hydrogen, $C_1$-$C_{20}$ linear or branched alkyl, $C_3$-$C_{20}$ cycloalkyl, $C_4$-$C_{20}$ cycloalkylalkyl, or $C_4$-$C_{20}$ alkylcycloalkyl.

19. The triphenylsulfonium salt compound according to claim 1, characterized in that: in the general formula (II), on two benzene rings directly connected with A, the connection position for S atom is the para-position of group A.

20. A photosensitive composition comprising the triphenylsulfonium salt compound according to claim 1.

* * * * *